(12) United States Patent
Gerardi et al.

(10) Patent No.: US 11,896,711 B2
(45) Date of Patent: Feb. 13, 2024

(54) PROCESS OF MAKING NANOEMULSION

(71) Applicant: NICOVENTURES TRADING LIMITED, London (GB)

(72) Inventors: Anthony Richard Gerardi, Winston-Salem, NC (US); Thomas H. Poole, Winston-Salem, NC (US); Steven Lee Alderman, Lewisville, NC (US)

(73) Assignee: NICOVENTURES TRADING LIMITED, London (GB)

( * ) Notice: Subject to any disclaimer, the term of this patent is extended or adjusted under 35 U.S.C. 154(b) by 32 days.

(21) Appl. No.: 17/187,973

(22) Filed: Mar. 1, 2021

(65) Prior Publication Data
US 2021/0177739 A1    Jun. 17, 2021

Related U.S. Application Data

(63) Continuation of application No. PCT/IB2020/061345, filed on Dec. 2, 2020.
(Continued)

(51) Int. Cl.
| A61K 9/16 | (2006.01) |
| A61K 9/20 | (2006.01) |
| A61K 9/00 | (2006.01) |
| A61K 31/352 | (2006.01) |
| A24B 15/30 | (2006.01) |

(Continued)

(52) U.S. Cl.
CPC .............. *A61K 9/009* (2013.01); *A24B 13/00* (2013.01); *A24B 15/16* (2013.01); *A61K 9/006* (2013.01); *A61K 9/1075* (2013.01); *A61K 31/05* (2013.01); *A61K 47/02* (2013.01); *A61K 47/10* (2013.01); *A61K 47/12* (2013.01); *A61K 47/14* (2013.01); *A61K 47/24* (2013.01); *A61K 47/38* (2013.01); *A61K 47/44* (2013.01)

(58) Field of Classification Search
None
See application file for complete search history.

(56) References Cited

U.S. PATENT DOCUMENTS

| 5,417,229 A | 5/1995 | Summers et al. |
| 6,138,683 A | 10/2000 | Hersh et al. |

(Continued)

FOREIGN PATENT DOCUMENTS

| CA | 3040513 | 10/2020 |
| CN | 103005680 | 4/2013 |

(Continued)

OTHER PUBLICATIONS

Robichaud Meagan et al., "Tobacco companies introduce 'tobacco free' nicotine pouches", *Tob Control 2019*, Nov. 21, 2019, 1-2, National Library of Medicine, doi:10.1136/tobaccocontrol-2019-055321.

*Primary Examiner* — Kyung S Chang
(74) *Attorney, Agent, or Firm* — Womble Bond Dickinson (US) LLP

(57) ABSTRACT

The disclosure provides a nanoemulsion including an oil phase containing at least one cannabinoid and a water phase; wherein at least one of the oil phase and the water phase includes one or more emulsifying agents; and wherein the zeta potential of the nanoemulsion is less than about −10 mV. Further provided are processes for preparing such nanoemulsions.

18 Claims, 1 Drawing Sheet

Related U.S. Application Data

(60) Provisional application No. 62/945,485, filed on Dec. 9, 2019.

(51) Int. Cl.
*A61K 31/05* (2006.01)
*A61K 9/107* (2006.01)
*A61K 47/24* (2006.01)
*A61K 47/10* (2017.01)
*A24B 15/16* (2020.01)
*A61K 47/02* (2006.01)
*A61K 47/38* (2006.01)
*A61K 47/44* (2017.01)
*A61K 47/14* (2017.01)
*A24B 13/00* (2006.01)
*A61K 47/12* (2006.01)

(56) References Cited

U.S. PATENT DOCUMENTS

| | | |
|---|---|---|
| 6,730,330 B2 | 5/2004 | Whittle et al. |
| 6,845,777 B2 | 1/2005 | Pera |
| 6,958,143 B2 | 10/2005 | Choi et al. |
| 7,032,601 B2 | 4/2006 | Atchley et al. |
| 7,056,541 B1 | 6/2006 | Stahl et al. |
| 7,507,427 B2 | 3/2009 | Andersen et al. |
| 7,569,274 B2 | 8/2009 | Besse et al. |
| 7,810,507 B2 | 10/2010 | Dube et al. |
| 7,833,555 B2 | 11/2010 | Andersen et al. |
| 7,861,728 B2 | 1/2011 | Holton, Jr. et al. |
| 7,900,637 B2 | 3/2011 | Fagerstrom et al. |
| 7,950,399 B2 | 5/2011 | Winterson et al. |
| 8,069,861 B2 | 12/2011 | Sinclair |
| 8,119,173 B2 | 2/2012 | Cheng et al. |
| 8,124,147 B2 | 2/2012 | Cheng et al. |
| 8,293,295 B2 | 10/2012 | Andersen et al. |
| 8,336,557 B2 | 12/2012 | Kumar et al. |
| 8,343,532 B2 | 1/2013 | Dam et al. |
| 8,424,541 B2 | 4/2013 | Crawford et al. |
| 8,469,036 B2 | 6/2013 | Williams et al. |
| 8,469,037 B2 | 6/2013 | Liu et al. |
| 8,529,875 B2 | 9/2013 | Andersen |
| 8,529,914 B2 | 9/2013 | Fuisz et al. |
| 8,545,870 B2 | 10/2013 | Dupinay et al. |
| 8,591,967 B2 | 11/2013 | Andersen et al. |
| 8,613,285 B2 | 12/2013 | Fuisz |
| 8,627,828 B2 | 1/2014 | Strickland et al. |
| 8,642,016 B2 | 2/2014 | Chau et al. |
| 8,714,163 B2 | 5/2014 | Kumar et al. |
| 8,741,348 B2 | 6/2014 | Hanson et al. |
| 8,747,562 B2 | 6/2014 | Mishra et al. |
| 8,828,361 B2 | 9/2014 | Anderson |
| 8,833,378 B2 | 9/2014 | Axelsson et al. |
| 8,846,075 B2 | 9/2014 | Johnson et al. |
| 8,858,984 B2 | 10/2014 | Dam et al. |
| 8,863,755 B2 | 10/2014 | Zhuang et al. |
| 8,871,243 B2 | 10/2014 | Fankhauser et al. |
| 8,931,493 B2 | 1/2015 | Sebastian et al. |
| 8,945,593 B2 | 2/2015 | LoCoco et al. |
| 8,978,661 B2 | 3/2015 | Atchley et al. |
| 8,992,974 B2 | 3/2015 | McCarty |
| 9,027,567 B2 | 5/2015 | Gee et al. |
| 9,039,839 B2 | 5/2015 | Beeson et al. |
| 9,044,035 B2 | 6/2015 | Jackson et al. |
| 9,084,439 B2 | 7/2015 | Holton, Jr. |
| 9,155,321 B2 | 10/2015 | Cantrell et al. |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,204,667 B2 | 12/2015 | Cantrell et al. |
| 9,237,768 B2 | 1/2016 | Carroll et al. |
| 9,265,724 B2 | 2/2016 | Murty et al. |
| 9,358,296 B2 | 6/2016 | McCarty |
| 9,372,033 B2 | 6/2016 | Lampe et al. |
| 9,386,800 B2 | 7/2016 | Sebastian et al. |
| 9,402,414 B2 | 8/2016 | Griscik et al. |
| 9,402,809 B2 | 8/2016 | Axelsson et al. |
| 9,414,624 B2 | 8/2016 | Carroll et al. |
| 9,420,825 B2 | 8/2016 | Beeson et al. |
| 9,468,233 B2 | 10/2016 | Macko et al. |
| 9,474,303 B2 | 10/2016 | Holton, Jr. |
| 9,521,864 B2 | 12/2016 | Gao et al. |
| 9,565,867 B2 | 2/2017 | Wittorff et al. |
| 9,629,392 B2 | 4/2017 | Holton, Jr. |
| 9,635,881 B2 | 5/2017 | Sjogren et al. |
| 9,675,102 B2 | 6/2017 | Hunt et al. |
| 9,730,911 B2 | 8/2017 | Verzura et al. |
| 9,763,928 B2 | 9/2017 | Duggins et al. |
| 9,775,376 B2 | 10/2017 | Cantrell et al. |
| 9,801,409 B1 | 10/2017 | Smith |
| 9,833,408 B1 | 12/2017 | Greenspoon |
| 9,848,634 B2 | 12/2017 | Fuisz |
| 9,854,830 B2 | 1/2018 | Gao et al. |
| 9,884,015 B2 | 2/2018 | Gao et al. |
| 9,907,748 B2 | 3/2018 | Borschke et al. |
| 9,925,145 B2 | 3/2018 | Hubinette et al. |
| 9,930,909 B2 | 4/2018 | Gao et al. |
| 9,999,243 B2 | 6/2018 | Gao et al. |
| 10,028,919 B2 | 7/2018 | Kaufman |
| 10,039,309 B2 | 8/2018 | Carroll et al. |
| 10,045,976 B2 | 8/2018 | Fusco et al. |
| 10,092,715 B2 | 10/2018 | Axelsson et al. |
| 10,130,120 B2 | 11/2018 | Mishra et al. |
| 10,143,230 B2 | 12/2018 | Mishra et al. |
| 10,149,850 B2 | 12/2018 | Mishra et al. |
| 10,172,810 B2 | 1/2019 | McCarty |
| 10,195,159 B2 | 2/2019 | Whittle et al. |
| 10,244,786 B2 | 4/2019 | Gao et al. |
| 10,334,873 B2 | 7/2019 | Mishra et al. |
| 10,357,054 B2 | 7/2019 | Marshall et al. |
| 10,375,984 B2 | 8/2019 | Hernandez Garcia et al. |
| 10,390,557 B2 | 8/2019 | Borjesson et al. |
| 10,426,726 B2 | 10/2019 | Neergaard |
| 10,463,070 B2 | 11/2019 | Carroll et al. |
| 10,532,046 B2 | 1/2020 | Rogers et al. |
| 10,543,205 B2 | 1/2020 | Wittorff et al. |
| 10,575,550 B2 | 3/2020 | Sengupta et al. |
| 10,986,859 B2 | 4/2021 | Gerardi et al. |
| 11,052,047 B2 | 6/2021 | Wittorff |
| 11,058,633 B2 | 7/2021 | Wittorff |
| 11,096,412 B2 | 8/2021 | Stahl et al. |
| 2004/0118422 A1 | 6/2004 | Lundin et al. |
| 2005/0191343 A1 | 9/2005 | Liang |
| 2007/0031539 A1 | 2/2007 | Calton |
| 2008/0081071 A1 | 4/2008 | Sanghvi et al. |
| 2008/0166395 A1 | 7/2008 | Roush |
| 2008/0286340 A1 | 11/2008 | Andersson et al. |
| 2008/0286341 A1 | 11/2008 | Andersson et al. |
| 2009/0023819 A1 | 1/2009 | Axelsson |
| 2009/0065013 A1 | 3/2009 | Essen et al. |
| 2009/0253754 A1 | 10/2009 | Selmin et al. |
| 2009/0301504 A1 | 12/2009 | Worthen et al. |
| 2010/0004294 A1 | 1/2010 | Axelsson et al. |
| 2010/0061940 A1 | 3/2010 | Axelsson et al. |
| 2010/0187143 A1 | 7/2010 | Essen et al. |
| 2010/0260690 A1 | 10/2010 | Kristensen et al. |
| 2010/0294292 A1 | 11/2010 | Hodin et al. |
| 2011/0139164 A1 | 6/2011 | Mua et al. |
| 2011/0220130 A1 | 9/2011 | Mua et al. |
| 2011/0268809 A1 | 11/2011 | Brinkley et al. |
| 2012/0031415 A1 | 2/2012 | Essen et al. |
| 2012/0037175 A1 | 2/2012 | Cantrell et al. |
| 2013/0078307 A1 | 3/2013 | Holton, Jr. et al. |
| 2013/0118512 A1 | 5/2013 | Jackson et al. |
| 2013/0152953 A1 | 6/2013 | Mua et al. |
| 2013/0177646 A1 | 7/2013 | Hugerth et al. |
| 2013/0206150 A1 | 8/2013 | Duggins et al. |
| 2013/0251779 A1 | 9/2013 | Svandal et al. |
| 2013/0340773 A1 | 12/2013 | Sebastian et al. |
| 2014/0130813 A1 | 5/2014 | Strehle |
| 2014/0154301 A1 | 6/2014 | Chau et al. |
| 2014/0255452 A1 | 9/2014 | Reddick et al. |

(56) References Cited

U.S. PATENT DOCUMENTS

| | | | |
|---|---|---|---|
| 2015/0068544 A1 | 3/2015 | Moldoveanu et al. | |
| 2015/0068545 A1 | 3/2015 | Moldoveanu et al. | |
| 2015/0071972 A1 | 3/2015 | Holton, Jr. et al. | |
| 2015/0096573 A1 | 4/2015 | Gao et al. | |
| 2015/0096574 A1 | 4/2015 | Gao et al. | |
| 2015/0096576 A1 | 4/2015 | Gao et al. | |
| 2015/0110924 A1* | 4/2015 | Bromley | A23L 33/12 426/555 |
| 2015/0296868 A1 | 10/2015 | Sutton | |
| 2016/0000140 A1 | 1/2016 | Sebastian et al. | |
| 2016/0015703 A1 | 1/2016 | Chronakis et al. | |
| 2016/0073676 A1 | 3/2016 | Cantrell et al. | |
| 2016/0073689 A1 | 3/2016 | Sebastian et al. | |
| 2016/0157515 A1 | 6/2016 | Chapman et al. | |
| 2016/0192703 A1 | 7/2016 | Sebastian et al. | |
| 2016/0199299 A1 | 7/2016 | Uren | |
| 2017/0000744 A1* | 1/2017 | Kaufman | A61K 9/006 |
| 2017/0007594 A1 | 1/2017 | Borschke | |
| 2017/0157041 A1 | 6/2017 | Goldner | |
| 2017/0164651 A1 | 6/2017 | Mua et al. | |
| 2017/0165252 A1 | 6/2017 | Mua et al. | |
| 2017/0172995 A1 | 6/2017 | Repaka et al. | |
| 2017/0280764 A1 | 10/2017 | Sahlen et al. | |
| 2017/0290776 A1 | 10/2017 | Schobel et al. | |
| 2017/0312261 A1 | 11/2017 | Changoer et al. | |
| 2017/0318858 A1 | 11/2017 | Hodin et al. | |
| 2017/0368020 A1 | 12/2017 | Estey | |
| 2018/0042845 A1* | 2/2018 | Sinai | A61K 31/352 |
| 2018/0116998 A1 | 5/2018 | Sinai et al. | |
| 2018/0140007 A1 | 5/2018 | Aspgren et al. | |
| 2018/0140521 A1 | 5/2018 | Geonnotti et al. | |
| 2018/0140554 A1 | 5/2018 | Wittorff | |
| 2018/0153211 A1 | 6/2018 | Persson | |
| 2018/0235273 A1 | 8/2018 | Carroll et al. | |
| 2018/0255826 A1 | 9/2018 | Persson et al. | |
| 2018/0257801 A1 | 9/2018 | Persson | |
| 2018/0303791 A1 | 10/2018 | Sinai et al. | |
| 2019/0037909 A1 | 2/2019 | Greenbaum et al. | |
| 2019/0060225 A1 | 2/2019 | Mandel | |
| 2019/0174812 A1 | 6/2019 | Nielsen et al. | |
| 2019/0201347 A1 | 7/2019 | Davis et al. | |
| 2019/0247325 A1 | 8/2019 | Kleidon | |
| 2019/0248987 A1 | 8/2019 | Moolman et al. | |
| 2019/0255035 A1 | 8/2019 | Bruun | |
| 2020/0022945 A1 | 1/2020 | Swartout | |
| 2020/0037638 A1 | 2/2020 | Faraci et al. | |
| 2020/0128870 A1 | 4/2020 | Hassler et al. | |
| 2020/0138706 A1 | 5/2020 | Rudraraju et al. | |
| 2020/0275689 A1 | 9/2020 | Lewerenz | |
| 2020/0297026 A1 | 9/2020 | Kannisto et al. | |
| 2020/0305496 A1 | 10/2020 | Gessesse | |
| 2020/0316012 A1 | 10/2020 | Schou | |
| 2020/0330423 A1 | 10/2020 | Brunn et al. | |
| 2021/0145818 A1 | 5/2021 | Docherty et al. | |
| 2021/0145841 A1 | 5/2021 | Docherty et al. | |
| 2021/0345656 A1 | 11/2021 | Nielsen et al. | |

FOREIGN PATENT DOCUMENTS

| | | |
|---|---|---|
| CN | 103263507 | 8/2013 |
| CN | 103494324 | 1/2014 |
| CN | 105192876 | 12/2015 |
| CN | 105595404 | 5/2016 |
| EP | 4094594 A1 | 11/2022 |
| WO | WO2002064109 A2 | 8/2002 |
| WO | WO 2004/000273 A1 | 12/2003 |
| WO | WO 2007/084587 A2 | 7/2007 |
| WO | WO 2008/046905 A1 | 4/2008 |
| WO | WO 2014/166994 A1 | 10/2014 |
| WO | WO201569763 A2 | 5/2015 |
| WO | WO 2015/090337 A1 | 6/2015 |
| WO | WO2015117011 A1 | 8/2015 |
| WO | WO2016147186 A1 | 9/2016 |
| WO | WO201861007 A1 | 4/2018 |
| WO | WO201894037 A1 | 5/2018 |
| WO | WO2018150182 A1 | 8/2018 |
| WO | WO2018211388 A1 | 11/2018 |
| WO | WO2018233781 A1 | 12/2018 |
| WO | WO2018233782 A1 | 12/2018 |
| WO | WO201934936 A2 | 2/2019 |
| WO | WO201936243 A1 | 2/2019 |
| WO | WO201952303 A1 | 3/2019 |
| WO | WO201957994 A1 | 3/2019 |
| WO | WO201967667 A1 | 4/2019 |
| WO | WO 2019/115778 A1 | 6/2019 |
| WO | WO2019135224 A1 | 7/2019 |
| WO | WO2019135225 A1 | 7/2019 |
| WO | WO2019159174 A1 | 8/2019 |
| WO | WO 2019/245639 | 12/2019 |

\* cited by examiner

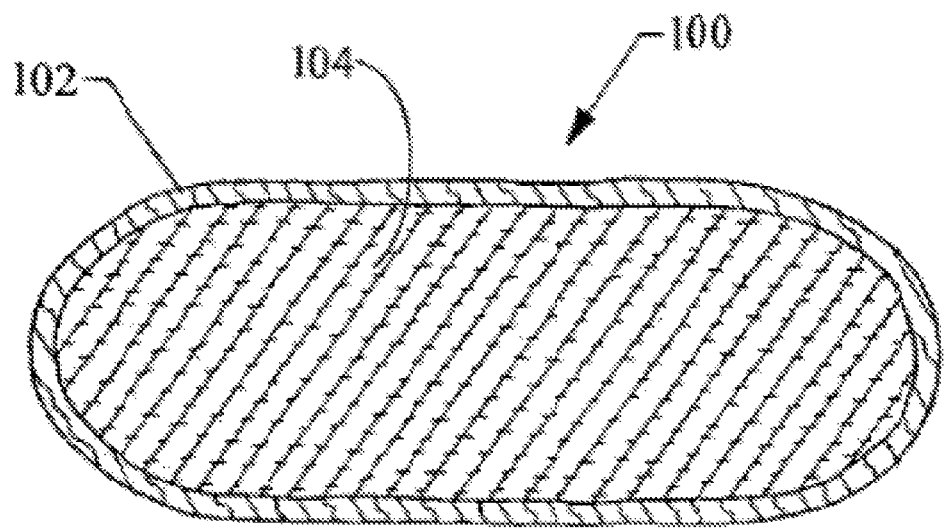

PROCESS OF MAKING NANOEMULSION

CROSS-REFERENCE TO RELATED APPLICATIONS

This application is a continuation of International Application No. PCT/IB2020/061345, filed Dec. 2, 2020, and claims priority to U.S. Provisional Application No. 62/945,485, filed on Dec. 9, 2019, which are incorporated herein by reference in their entirety and for all purposes.

FIELD

The present disclosure relates to process for preparing a nanoemulsion, as well as the nanoemulsion, oral products, pouched oral products and packages containing said nanoemulsion. In particular, the present disclosure relates to a process for preparing products, intended for human use. The products are configured for oral use and deliver an active ingredient during use. Such products include a cannabinoid or a product derived from a cannabinoid.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. No. 6,668,839 to Williams; U.S. Pat. No. 6,834,654 to Williams; U.S. Pat. No. 6,953,040 to Atchley et al.; U.S. Pat. No. 7,032,601 to Atchley et al.; and U.S. Pat. No. 7,694,686 to Atchley et al.; US Pat. Pub. Nos. 2004/0020503 to Williams; 2005/0115580 to Quinter et al.; 2006/0191548 to Strickland et al.; 2007/0062549 to Holton, Jr. et al.; 2007/0186941 to Holton, Jr. et al.; 2007/0186942 to Strickland et al.; 2008/0029110 to Dube et al.; 2008/0029116 to Robinson et al.; 2008/0173317 to Robinson et al.; 2008/0209586 to Neilsen et al.; 2009/0065013 to Essen et al.; and 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in US Patent App. Pub. Nos. 2008/0196730 to Engstrom et al.; 2008/0305216 to Crawford et al.; 2009/0293889 to Kumar et al.; 2010/0291245 to Gao et al; 2011/0139164 to Mua et al.; 2012/0037175 to Cantrell et al.; 2012/0055494 to Hunt et al.; 2012/0138073 to Cantrell et al.; 2012/0138074 to Cantrell et al.; 2013/0074855 to Holton, Jr.; 2013/0074856 to Holton, Jr.; 2013/0152953 to Mua et al.; 2013/0274296 to Jackson et al.; 2015/0068545 to Moldoveanu et al.; 2015/0101627 to Marshall et al.; and 2015/0230515 to Lampe et al., each of which is incorporated herein by reference.

All-white snus portions are growing in popularity, and offer a discrete and aesthetically pleasing alternative to traditional snus. Such modern "white" pouched products may include a bleached tobacco or may be tobacco-free.

It would be desirable to provide products configured for oral use which may deliver active ingredients to the consumer in an enjoyable form, such as in the form of a pouched product.

BRIEF SUMMARY

In accordance with some embodiments described herein, there is provided a process for preparing a nanoemulsion comprising at least one cannabinoid, the process comprising:

(a) providing an oil phase containing at least one cannabinoid;
(b) providing a water phase;
(c) combining the oil phase and water phase to form a macroemulsion; and
(d) treating the macroemulsion to form a nanoemulsion; wherein at least one of the oil phase and the water phase comprises one or more emulsifying agents.

In accordance with some embodiments described herein, there is provided a nanoemulsion comprising at least one cannabinoid, wherein the nanoemulsion is obtained or obtainable by a process comprising:

(a) providing an oil phase containing at least one cannabinoid;
(b) providing a water phase;
(c) combining the oil phase and water phase to form a macroemulsion; and
(d) treating the macroemulsion to form a nanoemulsion; wherein at least one of the oil phase and the water phase comprises one or more emulsifying agents.

In accordance with some embodiments described herein, there is provided a nanoemulsion comprising:

(a) an oil phase containing at least one cannabinoid;
(b) a water phase;
wherein at least one of the oil phase and the water phase comprises one or more emulsifying agents; and
wherein the zeta potential of the nanoemulsion is less than about −10 mV.

In accordance with some embodiments described herein, there is provided an oral product containing a nanoemulsion comprising at least one cannabinoid, wherein the nanoemulsion:

(a) is obtained or obtainable by a process as defined herein; or
(b) comprises:
(i) an oil phase containing at least one cannabinoid;
(ii) a water phase;
wherein at least one of the oil phase and the water phase comprises one or more emulsifying agents; and
wherein the zeta potential of the nanoemulsion is less than about −10 mV.

In accordance with some embodiments described herein, there is provided a pouched oral product comprising a saliva permeable pouch and an oral product as defined herein incorporated within the pouch.

In accordance with some embodiments described herein, there is provided a package containing an oral product as defined herein or at least one pouched oral product as defined herein.

The disclosure includes, without limitations, the following embodiments.

Embodiment 1: A process for preparing a nanoemulsion comprising at least one cannabinoid, the process comprising: (a) providing an oil phase containing at least one cannabinoid; (b) providing a water phase; (c) combining the oil phase and water phase to form a macroemulsion; and (d) treating the macroemulsion to form a nanoemulsion; wherein at least one of the oil phase and the water phase comprises one or more emulsifying agents.

Embodiment 2: A process according to embodiment 1, wherein (d) comprising sonicating the macroemulsion to form the nanoemulsion.

Embodiment 3: A process according to embodiment 1 or 2, wherein (d) comprises treating the macroemulsion in a homogenizer to form the nanoemulsion.

Embodiment 4: A process according to embodiment 3, wherein the homogenizer is a high pressure valve homogenizer, an ultrasonic jet homogenizer or an ultrasonic probe homogenizer.

Embodiment 5: A process according to embodiment 3 or 4, wherein the macroemulsion is passed through the homogenizer at a flow rate of from about 100 mL/min to about 9 L/min.

Embodiment 6: A process according to any one of embodiments 3 to 5, wherein the macroemulsion is passed through the homogenizer at a temperature of from about 20° C. to about 40° C.

Embodiment 7: A process according to any one of claims 1 to 6, wherein (d) comprises treating the macroemulsion in a microfluidizer to form the nanoemulsion.

Embodiment 8: A process according to any one of embodiments 1 to 7, wherein the process further comprises (a)(1) of heating the oil phase to a temperature of at least about 50° C. and dissolving the at least one cannabinoid therein.

Embodiment 9: A process according to embodiment 8, wherein (a)(1) comprises heating the oil phase to a temperature of from about 60° C. to about 85° C.

Embodiment 10: A process according to any one of embodiments 1 to 9, wherein the weight ratio of the oil to the at least one cannabinoid is from about 1:1 to about 10:1.

Embodiment 11: A process according to any one of embodiments 1 to 10, wherein the process further comprises (b)(1) combining the water phase with one or more emulsifying agents.

Embodiment 12: A process according to embodiment 11, wherein (b)(1) comprises combining the water phase with one or more emulsifying agents via high shear mixing.

Embodiment 13: A process according to any one of embodiments 1 to 12, wherein (c) comprises combining the oil phase and the water phase via high shear mixing to form the macroemulsion.

Embodiment 14: A process according to any one of embodiments 1 to 13, wherein (c) comprises combining the oil phase and the water phase in a weight ratio of from about 2:1 to about 1:10.

Embodiment 15: A process according to any one of embodiments 1 to 14, wherein the total HLB value of the one or more emulsifying agents is from about 11 to about 15.

Embodiment 16: A process according to any one of embodiments 1 to 15, wherein the one or more emulsifying agents is or comprises an emulsifying agent selected from the group consisting of stearamide MEA, glyceryl stearate (and) PEG-100 stearate, polysorbate 85, PEG-7 olivate, cetearyl glucoside, PEG-8 oleate, polyglyceryl-3 methylglucose distearate, oleth-10, oleth-10/polyoxyl 10 oleyl ether NF, ceteth-10, PEG-8 laurate, cocamide MEA, polysorbate 60, polysorbate 80, isosteareth-20, PEG-60 almond glycerides, PEG-20 methyl glucose sesquistearate, PEG-7 glyceryl cocoate, PEG-8 stearate, PEG-8 caprate, PEG-35 almond glycerides, PEG-6 laurate, laureth-7, steareth-10, isotrideceth-8, PEG-35 castor oil, isotrideceth-9, PEG-40 castor oil, ceteareth-12, laureth-9, PEG-40 hydrogenated castor oil, PEG-20 glyceryl isostearate, PEG-20 stearate, and mixtures thereof.

Embodiment 17: A process according to any one of embodiments 1 to 15, wherein the one or more emulsifying agents comprises a first emulsifying agent having an HLB value of from about 1 to about 9, and a second emulsifying agent having an HLB value of from about 10 to about 20.

Embodiment 18: A process according to embodiment 17, wherein the first emulsifying agent is selected from the group consisting of glycol distearate, sorbitan trioleate, sorbitan tristearate, sorbitan triisostearate, glyceryl isostearate, propylene glycol isostearate, glycol stearate, sorbitan sesquioleate, glyceryl stearate, lecithin, sorbitan oleate, sorbitan monostearate, sorbitan stearate, sorbitan isostearate, steareth-2, oleth-2, PEG-7 hydrogenated castor oil, laureth-2, sorbitan palmitate, laureth-3, glyceryl laurate, ceteth-2, PEG-30 dipolyhdroxystearate, glyceryl stearate SE, sorbitan stearate (and) sucrose cocoate, PEG-4 dilaurate, methyl glucose sesquistearate, PEG-8 dioleate, sorbitan laurate, PEG-40 sorbitan peroleate, and mixtures thereof.

Embodiment 19: A process according to embodiment 17 or 18, wherein the second emulsifying agent is selected from the group consisting of laureth-4, PEG-7 glyceryl cocoate, PEG-20 almond glycerides, PEG-25 hydrogenated castor oil, stearamide MEA, glyceryl stearate (and) PEG-100 stearate, polysorbate 81, polysorbate 85, polysorbate 65, PEG-7 glyceryl cocoate, PEG-8 stearate, PEG-8 caprate, PEG-35 almond glycerides, PEG-6 laurate, laureth-7, steareth-10, isotrideceth-8, PEG-35 castor oil, isotrideceth-9, PEG-40 castor oil, ceteareth-12, laureth-9, PEG-40 hydrogenated castor oil, PEG-20 glyceryl isostearate, PEG-20 stearate, PEG-40 sorbitan perisostearate, PEG-7 olivate, cetearyl glucoside, PEG-8 oleate, polyglyceryl-3 methylglucose distearate, oleth-10, oleth-10/polyoxyl 10 oleyl ether NF, ceteth-10, PEG-8 laurate, cocamide MEA, polysorbate 60, polysorbate 80, isosteareth-20, PEG-60 almond glycerides, PEG-20 methyl glucose sesquistearate, ceteareth-20, oleth-20, steareth-20, steareth-21, ceteth-20, isoceth-20, polysorbate 20, polysorbate 40, ceteareth-25, ceteareth-30, PEG-30 stearate, laureth-23, PEG-75 lanolin, polysorbate 20, PEG-40 stearate, PEG-100 stearate, steareth-100, PEG-80 sorbitan laurate, polyoxyethylene stearate (e.g., polyoxyethylene (40) stearate), polyoxyethylene ether, and mixtures thereof.

Embodiment 20: A process according to any one of embodiments 1 to 19, wherein the cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), tetrahydrocannabivarinic acid (THCV A), and mixtures thereof.

Embodiment 21: A process according to any one of embodiments 1 to 20, wherein the cannabinoid comprises cannabidiol.

Embodiment 22: A nanoemulsion comprising at least one cannabinoid, wherein the nanoemulsion is obtained or obtainable by a process comprising: (a) providing an oil phase containing at least one cannabinoid; (b) providing a water phase; (c) combining the oil phase and water phase to form a macroemulsion; and (d) treating the macroemulsion to form a nanoemulsion; wherein at least one of the oil phase and the water phase comprises one or more emulsifying agents.

Embodiment 23: A nanoemulsion according to embodiment 22, wherein the zeta potential of the nanoemulsion is less than about −10 mV.

Embodiment 24: A nanoemulsion according to embodiment 22 or 23, wherein the nanoemulsion comprises droplets of the oil phase dispersed in the water phase, the droplets having an average diameter of from about 1 nm to about 200 nm.

Embodiment 25: A nanoemulsion comprising: (a) an oil phase containing at least one cannabinoid; (b) a water phase; wherein at least one of the oil phase and the water phase comprises one or more emulsifying agents; and wherein the zeta potential of the nanoemulsion is less than about −10 mV.

Embodiment 26: An oral product containing a nanoemulsion comprising at least one cannabinoid, wherein the nanoemulsion is: (a) obtained or obtainable by a process as defined in any one of embodiments 1 to 21; or (b) as defined in any one of embodiments 22 to 25.

Embodiment 27: An oral product according to embodiment 26 further comprising a filler.

Embodiment 28: An oral product according to claim 26 or 27, wherein the water activity of the oral product is no greater than about 0.85.

Embodiment 29: A pouched oral product comprising a saliva permeable pouch and an oral product as defined in any one of embodiments 26 to 28 incorporated within the pouch.

Embodiment 30: A package containing an oral product as defined in any one of embodiments 26 to 28 or at least one pouched oral product as defined in c embodiment 29.

Embodiment 31: A process, nanoemulsion, product, or package according to any one of embodiments 1 to 30, wherein the cannabinoid is replaced in whole or in part with a cannabimimetic.

These and other features, aspects, and advantages of the disclosure will be apparent from a reading of the following detailed description, which are briefly described below. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

BRIEF DESCRIPTION OF THE DRAWINGS

Having thus described aspects of the disclosure in the foregoing general terms, reference will now be made to the accompanying drawings, which are not necessarily drawn to scale. The drawings are exemplary only, and should not be construed as limiting the disclosure. Embodiments of the invention will now be described, by way of example only, with reference to accompanying drawings, in which:

FIG. 1 is a cross-sectional view of a pouched product embodiment, taken across the width of the product, showing an outer pouch filled with a composition of the present disclosure.

DETAILED DESCRIPTION

As described herein, there is provided a process for preparing a nanoemulsion comprising at least one cannabinoid, the process comprising:

(a) providing an oil phase containing at least one cannabinoid;

(b) providing a water phase;

(c) combining the oil phase and water phase to form a macroemulsion; and (d) treating the macroemulsion to form a nanoemulsion; wherein at least one of the oil phase and the water phase comprises one or more emulsifying agents.

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

The processes and products as described herein comprise forming an nanoemulsion comprising a water phase and an oil phase, wherein the nanoemulsion comprises at least one cannabinoid. The relative amounts of the various components within the processes and products may vary, and typically are selected so as to provide the desired sensory and performance characteristics to the nanoemulsion or oral product containing the nanoemulsion. The example individual components of the product are described herein below.

Process

In accordance with some embodiments described herein, there is provided a process for preparing a nanoemulsion comprising at least one cannabinoid, the process comprising:

(a) providing an oil phase containing at least one cannabinoid;

(b) providing a water phase;

(c) combining the oil phase and water phase to form a macroemulsion; and (d) treating the macroemulsion to form a nanoemulsion; wherein at least one of the oil phase and the water phase comprises one or more emulsifying agents.

(a)

As described herein, (a) comprises providing an oil phase. The oil phase contains an oil in combination with at least one cannabinoid. Any suitable oil may be used as the oil phase in (a), including petroleum-based (e.g., mineral oil) and natural or naturally derived oils (e.g., from plant materials or animal sources). In some embodiments, the oil comprises mineral oil. In some embodiments, the oil comprises a long chain fatty acid, a monoacylglycerol, a diacylglycerol, a triacylglycerol, or a combination thereof, wherein the acyl group is a long chain fatty acid. As used herein, "long chain fatty acid" refers to a carboxylic ($CO_2H$) acid having an aliphatic carbon chain of from about 11 to about 21 carbon atoms. The aliphatic carbon chain may be straight or branched. The aliphatic carbon chain may be saturated (i.e., having all $sp^3$ carbon atoms), or may be unsaturated (i.e., having at least one site of unsaturation). As used herein, the term "unsaturated" refers to the presence of a carbon-carbon, $sp^2$ double bond in one or more positions within the aliphatic carbon chain. Unsaturated alkyl groups may be mono- or polyunsaturated. Representative long chain fatty acids include, but are not limited to, undecylic acid, undecanoic acid, lauric acid, tridecanoic acid, myristic acid, pentadecanoic acid, palmitic acid, margaric acid, stearic acid, nonadecanoic acid, arachidic acid, heneicosanoic acid, α-linolenic acid, stearidonic acid, eicosapentaenoic acid, cervonic acid, linoleic acid, linolelaidic acid, γ-linolenic acid, dihomo-γ-linolenic acid, and arachidonic acid.

In some embodiments, the oil comprises an acyl glycerol, such as a monoacylglycerol, a diacylglycerol, or a triacylglycerol, wherein the acyl group is a long chain fatty acid as described herein. In some embodiments, the oil comprises a triacylglycerol, wherein the acyl group is a long chain fatty acid as described herein. In some embodiments, the oil comprises polyunsaturated long chain fatty acids, or mono- di- or triacylglycerol containing polyunsaturated long chain fatty acids as the acyl component. The chain lengths of the fatty acids in naturally occurring triglycerides may vary, but is typically 16, 18, or 20 carbon atoms. In some embodiments, the concentration of polyunsaturated fatty acid (as free fatty acid or as e.g., triglycerides) in the oil can range from about 2% to 100% (w/w), such as from about 5% to 100% (w/w) or greater than 10%, e.g., 20%-80% (w/w).

In some embodiments, the oil may be made up of primarily long-chain triacylglycerols (LCTs). In some embodiments, the oil may comprise medium-chain triacylglycerols (MCTs) and/or short-chain triacylglycerols (SCTs). In some embodiments, the oil comprises castor oil, corn oil, coconut oil, cod liver oil, evening primrose oil, cottonseed oil, palm oil, rice bran oil, sesame oil, rapeseed oil, canola oil, cocoa butter, linseed oil, olive oil, peanut oil, soybean oil, safflower oil, flaxseed oil, sunflower oil, olive oil, or a combination thereof.

The amount of oil present within the final nanoemulsion can vary. In some embodiments, (a) comprises providing oil such that the final nanoemulsion contains the oil in an amount of from about 1% to about 80% by weight, such as from about 5% to about 60% by weight, such as from about 5% to about 50% by weight, such as from about 5% to about 30% by weight, such as from about 10% to about 20% by weight, based on the total weight of the emulsion.

As described herein, (a) comprises providing an oil phase that contains at least one cannabinoid. Cannabinoids are a class of natural or synthetic chemical compounds which act on cannabinoid receptors (i.e., CB1 and CB2) in cells that repress neurotransmitter release in the brain. Cannabinoids are cyclic molecules exhibiting particular properties such as the ability to easily cross the blood-brain barrier. Cannabinoids may be naturally occurring (Phytocannabinoids) from plants such as *cannabis*, (endocannabinoids) from animals, or artificially manufactured (synthetic cannabinoids). *Cannabis* species express at least 85 different phytocannabinoids, and these may be divided into subclasses, including cannabigerols, cannabichromenes, cannabidiols, tetrahydrocannabinols, cannabinols and cannabinodiols, and other cannabinoids, such as cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), and tetrahydrocannabivarinic acid (THCV A).

In some embodiments, the cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), tetrahydrocannabivarinic acid (THCV A), and mixtures thereof. In some embodiments, the cannabinoid comprises at least tetrahydrocannabinol (THC). In some embodiments, the cannabinoid is tetrahydrocannabinol (THC). In some embodiments, the cannabinoid comprises at least cannabidiol (CBD). In some embodiments, the cannabinoid is cannabidiol (CBD).

In some embodiments, the cannabinoid is cannabidiol (CBD) or a pharmaceutically acceptable salt thereof. In some embodiments, the cannabidiol is synthetic cannabidiol. In some embodiments, the cannabinoid is added to the emulsion in the form of an isolate. In some embodiments, the cannabidiol is added to the emulsion in the form of an isolate. An isolate is an extract from a plant, such as *cannabis*, where the active material of interest (in this case the cannabinoid, such as CBD) is present in a high degree of purity, for example greater than 95%, greater than 96%, greater than 97%, greater than 98%, or around 99% purity.

In some embodiments, the cannabinoid is an isolate of CBD in a high degree of purity, and the amount of any other cannabinoid in the nanoemulsion is no greater than about 1% by weight of the nanoemulsion, such as no greater than about 0.5% by weight of the nanoemulsion, such as no greater than about 0.1% by weight of the nanoemulsion, such as no greater than about 0.01% by weight of the nanoemulsion.

The choice of cannabinoid and the particular percentages thereof which may be present within the disclosed emulsion will vary depending upon the desired flavor, texture, and other characteristics of the emulsion and any product into which the emulsion is incorporated.

Alternatively, or in addition to the cannabinoid, the oral product can include a cannabimimetic, which is a class of compounds derived from plants other than *cannabis* that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids. Such compounds can be used in the same amounts and ratios noted herein for cannabinoids.

In some embodiments, (a) comprises contacting an oil with at least one cannabinoid in order to provide an oil phase containing at least one cannabinoid.

In some embodiments, (a) comprises mixing the oil with at least one cannabinoid. This mixing may further utilize high shear mixing, high pressure, high temperature, or the like. In some embodiments, (a) comprises heating the oil phase to a temperature of about 50° C. and dissolving the at least one cannabinoid therein. For example, the oil phase may be heated to a temperature of about 50° C. to about 90° C., such as from about 55° C. to about 85° C., such as from about 60° C. to about 85° C., such as from about 65° C. to about 85° C., such as from about 70° C. to about 85° C.

Therefore, in some embodiments, the process further comprises (a)(1) of heating the oil phase to a temperature of at least about 50° C. (such as from about 60° C. to about 85° C.) and dissolving the at least one cannabinoid therein.

In some embodiments, (a) comprises mixing the oil with the at least one cannabinoid (such as at a temperature of at least about 50° C.) for a period of from about 1 minute to about 60 minutes, such as from about 5 minutes to about 45 minutes, such as from about 10 minutes to about 30 minutes, such as from about 15 minutes to about 20 minutes. In some embodiments, (a) comprises mixing the oil with the at least one cannabinoid (such as at a temperature of at least about 50° C.) for a period of at least about 10 minutes.

In some embodiments, (a) comprises providing the oil phase, wherein the weight ratio of cannabinoid to oil in the oil phase is any suitable ratio for dispersing (or dissolving) the cannabinoid in the oil whilst providing an effective amount of the cannabinoid. In some embodiments, the weight ratio of cannabinoid to oil is from about 2:1 to about 1:20, such as from about 1:1 to about 1:10, such as from about 1:1 to about 1:5, such as about 1:2.

In some embodiments, the weight ratio of the oil to the at least one cannabinoid is from about 1:1 to about 10:1, such as from about 1:1 to about 5:1. As described herein, "the weight ratio of the oil to the at least one cannabinoid" refers to the weight ratio of the oil to the cannabinoid in the oil phase.

(b)
As described herein, (b) comprises providing a water phase (or "aqueous phase"). The water phase comprises at least water.

The water phase may also optionally comprise one or more additives, such as preservatives, humectants, emulsifying agents, flavoring agents, or the like.

Water may be present as, for example, purified or ultrapure water, saline, buffered saline, or a buffered aqueous phase. In some embodiments, a further hydrophilic, water soluble component may be added to the water, including short chain mono-, di-, and polyhydric alcohols, (e.g., ethanol, benzyl alcohol, glycerol, propylene glycol, propylene carbonate, polyethylene glycol with an average molecular weight of about 200 to about 10,000, diethylene glycol monoethyl ether, and combinations thereof).

The water content of the final emulsion may vary according to the desired properties. In some embodiments, (b) comprises providing water in an amount such that the final water content of the nanoemulsion will be from about 10% to about 90% by weight, based on the total weight of the emulsion. In some embodiments, the water content is from about 15% to about 60% by weight, such as from about 20% to about 50% by weight, such as from about 25% to about 40% by weight, based on the total weight of the emulsion.

The water phase may contain one or more water-soluble or -dispersible additives therein. Therefore, in some embodiments, (b) further comprises contacting water with one or more additives in order to provide the water phase.

In some embodiments, the process further comprises (b)(1) of combining water with one or more emulsifying agents. The water phase may thus comprise water in combination with one or more emulsifying agents.

It is noted that, whilst the following passage describes the inclusion of one or more emulsifying agents in the water phase, such emulsifying agent(s) may also equally be included in the oil phase. As such, one or more emulsifying agents may be included in the oil phase, the water phase and/or both the oil phase and the water phase.

By "emulsifying agent" is meant a substance which aids in the formation and stabilization of emulsions by promoting dispersion of hydrophobic and hydrophilic (e.g., oil and water) components. In general, emulsifying agents are amphiphilic molecules chosen from, for example, nonionic and ionic amphiphilic molecules. The expression "amphiphilic molecule" means any molecule of bipolar structure comprising at least one hydrophobic portion and at least one hydrophilic portion and having the property of reducing the surface tension of water and of reducing the interface tension between water and an oily phase. Emulsifying agents/amphiphilic molecules as provided herein are also referred to as, for example, surfactants and emulsifiers.

In some embodiments, the emulsifying agent is selected from the group consisting of small molecule surfactants, phospholipids, proteins, polysaccharides, and mixtures thereof. In some embodiments, the one or more emulsifying agents is selected from the group consisting of polyethylene glycol esters of fatty acids, propylene glycol esters of fatty acids, polysorbates, polyglycerol esters of fatty acids, polyglycerol polyricinoleate, sorbitan esters of fatty acid, sucrose esters of fatty acids, lecithins, enzyme treated lecithins, glycerin fatty acids esters, acetic acid esters of monoglycerides, lactic acid esters of monoglycerides, citric acid esters of monoglycerides, succinic acid esters of monoglycerides, diacetyl tartaric acid esters of monoglycerides, calcium stearoyl di lactate, chitin and chitosan derivatives, nature and modified starches, nature and modified hydrocolloids, nature and modified polysaccharides, nature and modified celluloses, nature and modified proteins, synthetic amphiphilic polymers, and mixtures thereof.

In some embodiments, the one or more emulsifying agents is selected from the group consisting of polyethylene glycol esters of fatty acids, propylene glycol esters of fatty acids, polysorbates, polyglycerol esters of fatty acids, polyglycerol polyricinoleate, sorbitan esters of fatty acid, sucrose esters of fatty acids, lecithins, glycerin fatty acids esters, acetic acid esters of monoglycerides, lactic acid esters of monoglycerides, citric acid esters of monoglycerides, succinic acid esters of monoglycerides, diacetyl tartaric acid esters of monoglycerides, calcium stearoyl di lactate, and mixtures thereof.

In some embodiments, the one or more emulsifying agents is selected from the group consisting of polyethylene glycol esters of fatty acids, polyethylene glycol esters of lecithin and mixtures thereof.

In some embodiments, the one or more emulsifying agents is selected from the group consisting of glycol distearate, sorbitan trioleate, sorbitan tristearate, sorbitan triisostearate, glyceryl isostearate, propylene glycol isostearate, glycol stearate, sorbitan sesquioleate, glyceryl stearate, lecithin, sorbitan oleate, sorbitan monostearate, sorbitan stearate, sorbitan isostearate, steareth-2, oleth-2, PEG-7 hydrogenated castor oil, laureth-2, sorbitan palmitate, laureth-3, glyceryl laurate, ceteth-2, PEG-30 dipolyhdroxystearate, glyceryl stearate SE, sorbitan stearate (and) sucrose cocoate, PEG-4 dilaurate, methyl glucose sesquistearate, PEG-8 dioleate, sorbitan laurate, PEG-40 sorbitan peroleate, laureth-4, PEG-7 glyceryl cocoate, PEG-20 almond glycerides, PEG-25 hydrogenated castor oil, stearamide MEA, glyceryl stearate (and) PEG-100 stearate, polysorbate 81, polysorbate 85, polysorbate 65, PEG-7 glyceryl cocoate, PEG-8 stearate, PEG-8 caprate, PEG-35 almond glycerides, PEG-6 laurate, laureth-7, steareth-10, isotrideceth-8, PEG-35 castor oil, isotrideceth-9, PEG-40 castor oil, ceteareth-12, laureth-9, PEG-40 hydrogenated castor oil, PEG-20 glyceryl isostearate, PEG-20 stearate, PEG-40 sorbitan perisostearate, PEG-7 olivate, cetearyl glucoside, PEG-8 oleate, polyglyceryl-3 methylglucose distearate, oleth-10, oleth-10/polyoxyl 10 oleyl ether NF, ceteth-10, PEG-8 laurate, cocamide MEA, polysorbate 60, polysorbate 80, isosteareth-20, PEG-60 almond glycerides, PEG-20 methyl glucose sesquistearate, ceteareth-20, oleth-20, steareth-20, steareth-21, ceteth-20, isoceth-20, polysorbate 20, polysorbate 40, ceteareth-25, ceteareth-30, PEG-30 stearate, laureth-23, PEG-75 lanolin, polysorbate 20, PEG-40 stearate, PEG-100 stearate, steareth-100, PEG-80 sorbitan laurate, polyoxyethylene stearate (e.g., polyoxyethylene (40) stearate), polyoxyethylene ether, and mixtures thereof.

In some embodiments, the one or more emulsifying agents have an overall HLB value in the range of from about 10 to about 15, such as from about 11 to about 15, such as from about 11 to about 14, such as from about 11 to about 13.5. As will be understood by one skilled in the art, HLB is the hydrophilic-lipophilic balance of an emulsifying agent or surfactant is a measure of the degree to which it is hydrophilic or lipophilic. The HLB value may be determined by calculating values for the different regions of the molecule, as described by Griffin in Griffin, William C. (1949), "Classification of Surface-Active Agents by 'HLB'" (PDF), Journal of the Society of Cosmetic Chemists, 1 (5): 311-26 and Griffin, William C. (1954), "Calculation of HLB Values of Non-Ionic Surfactants" (PDF), Journal of the Society of Cosmetic Chemists, 5 (4): 249-56, and by Davies in Davies JT (1957), "A quantitative kinetic theory of emulsion type, I. Physical chemistry of the emulsifying agent" (PDF), Gas/Liquid and Liquid/Liquid Interface, Proceedings of the International Congress of Surface Activity, pp. 426-38. HLB value may be determined in accordance with the industry standard text book, namely "The HLB SYSTEM, a time-saving guide to emulsifier selection" ICI Americas Inc., Published 1976 and Revised, March, 1980. The HLB values of the emulsifiers described herein were determined in accordance with this standard method.

In some embodiments, the one or more emulsifying agents have an HLB value of from about 11 to about 15. In some embodiments, the one or more emulsifying agents have an HLB value of from about 11 to about 13.5. In some embodiments, the overall HLB value of the one or more emulsifying agents present in the nanoemulsion is from about 11 to about 15, such as from about 11 to about 13.5.

In some embodiments, the nanoemulsion comprises an emulsifying agent having an HLB value of from about 11 to about 15, wherein the emulsifying agent is selected from the group consisting of: stearamide MEA, glyceryl stearate (and) PEG-100 stearate, polysorbate 85, PEG-7 olivate, cetearyl glucoside, PEG-8 oleate, polyglyceryl-3 methylglucose distearate, oleth-10, oleth-10/polyoxyl 10 oleyl ether NF, ceteth-10, PEG-8 laurate, cocamide MEA, polysorbate 60, polysorbate 80, isosteareth-20, PEG-60 almond glycerides, PEG-20 methyl glucose sesquistearate, PEG-7 glyceryl cocoate, PEG-8 stearate, PEG-8 caprate, PEG-35 almond glycerides, PEG-6 laurate, laureth-7, steareth-10, isotrideceth-8, PEG-35 castor oil, isotrideceth-9, PEG-40 castor oil, ceteareth-12, laureth-9, PEG-40 hydrogenated castor oil, PEG-20 glyceryl isostearate, PEG-20 stearate, and mixtures thereof.

In some embodiments, the nanoemulsion comprises at least two emulsifying agents which have different HLB values. In some embodiments, the nanoemulsion comprises a first emulsifying agent with a low HLB value, and a second emulsifying agent with a high HLB value. In some embodiments, the nanoemulsion comprises a first emulsifying agent having an HLB value of from about 1 to about 9 (such as from about 2 to 9, such as from about 3 to 9, such as from about 3 to 8) and a second emulsifying agent having an HLB value of from about 10 to about 20 (such as from about 10 to 18, such as from about 11 to 17). In some embodiments, the overall (i.e., combined) HLB value of the first and second emulsifying agents is from about 11 to about 15, such as from about 11 to about 13.5.

The first emulsifying agent having an HLB value of from about 1 to about 9 may be selected from any suitable emulsifying agent having such an HLB value. For example, the first emulsifying agent may be an emulsifier having a HLB value of from about 1 to about 9 selected from mono and diglycerydes of fatty acid including glyceryl stearate and glyceryl oleate; fatty acid esters of C12-C22 fatty alcohols including fatty acid esters of cetyl alcohol and fatty acid esters of stearoyl alcohol, mixtures of fatty acid esters of cetyl alcohol and fatty acid esters of stearoyl alcohol, mixtures of fatty acid esters of cetyl alcohol and fatty acid esters of stearoyl alcohol wherein the fatty acids are derived from olive oil (such as cetearyl olivate), fatty acid esters of sorbitol including sorbitan oleate, fatty acid esters of sorbitol wherein the fatty acids are derived from olive oil (such as sorbitan olivate or cetearyl olivate), and mixtures thereof.

In some embodiments, the first emulsifying agent is an emulsifier having a HLB value of from about 1 to 9 selected from mono and diglycerydes of fatty acid, fatty acid esters of C12-C22 fatty alcohols, fatty acid esters of sorbitol, and mixtures thereof. In some embodiments, the first emulsifying agent is selected from the group consisting of glycol distearate, sorbitan trioleate, sorbitan tristearate, sorbitan triisostearate, glyceryl isostearate, propylene glycol isostearate, glycol stearate, sorbitan sesquioleate, glyceryl stearate, lecithin (such as soy lecithin), sorbitan oleate, sorbitan monostearate, sorbitan stearate, sorbitan isostearate, steareth-2, oleth-2, PEG-7 hydrogenated castor oil, laureth-2, sorbitan palmitate, laureth-3, glyceryl laurate, ceteth-2, PEG-30 dipolyhdroxystearate, glyceryl stearate SE, sorbitan stearate (and) sucrose cocoate, PEG-4 dilaurate, methyl glucose sesquistearate, PEG-8 dioleate, sorbitan laurate, PEG-40 sorbitan peroleate, and mixtures thereof.

In some embodiments, the first emulsifying agent is or comprises lecithin. In some embodiments, the first emulsifying agent is or comprises soy lecithin.

The second emulsifying agent may be selected from any suitable emulsifying agent having an HLB value of from about 10 to about 20. In some embodiments, the second emulsifying agent is an emulsifier having a HLB value of from 10 to 20 selected from fatty acid esters of polyethylene glycol, such as fatty acid esters of polyethylene glycol wherein the fatty acids are derived from coconut oil (including PEG 7), fatty acid esters of polyglycerol including fatty acid esters of polyglycerol and oleic acid (such as polyglyceryl 10 oleate), and mixtures thereof. In some embodiments, the second emulsifying agent is an emulsifier having a HLB value of from 10 to 20 selected from fatty acid esters of polyethylene glycol, fatty acid esters of polyglycerol, and mixtures thereof. In some embodiments, the second emulsifying agent may be selected from the group consisting of laureth-4, PEG-7 glyceryl cocoate, PEG-20 almond glycerides, PEG-25 hydrogenated castor oil, stearamide MEA, glyceryl stearate (and) PEG-100 stearate, polysorbate 81, polysorbate 85, polysorbate 65, PEG-7 glyceryl cocoate, PEG-8 stearate, PEG-8 caprate, PEG-35 almond glycerides, PEG-6 laurate, laureth-7, steareth-10, isotrideceth-8, PEG-35 castor oil, isotrideceth-9, PEG-40 castor oil, ceteareth-12, laureth-9, PEG-40 hydrogenated castor oil, PEG-20 glyceryl isostearate, PEG-20 stearate, PEG-40 sorbitan perisostearate, PEG-7 olivate, cetearyl glucoside, PEG-8 oleate, polyglyceryl-3 methylglucose distearate, oleth-10, oleth-10/polyoxyl 10 oleyl ether NF, ceteth-10, PEG-8 laurate, cocamide MEA, polysorbate 60, polysorbate 80, isosteareth-20, PEG-60 almond glycerides, PEG-20 methyl glucose sesquistearate, ceteareth-20, oleth-20, steareth-20, steareth-21, ceteth-20, isoceth-20, polysorbate 20, polysorbate 40, ceteareth-25, ceteareth-30, PEG-30 stearate, laureth-23, PEG-75 lanolin, polysorbate 20, PEG-40 stearate, PEG-100 stearate, steareth-100, PEG-80 sorbitan laurate, polyoxyethylene stearate (e.g., polyoxyethylene (40) stearate), polyoxyethylene ether, and mixtures thereof.

In some embodiments, the second emulsifying agent is or comprises polyoxyethylene stearate (e.g., polyoxyethylene (40) stearate).

In some embodiments, the emulsifying agent is or comprises a combination of lecithin (e.g., soy lecithin) and polyoxyethylene stearate (e.g., polyoxyethylene (40) stearate).

In some embodiments, the one or more emulsifying agents comprises neutral, positively charged, or negatively charged natural or synthetic phospholipids molecules. Phospholipids are made up of two fatty acid tails and a phosphate group head, connected via a third molecule, glycerol. Non-limiting examples of natural phospholipids including lecithin (such as soy lecithin and/or egg lecithin), phosphatidyl choline-enriched lecithin, phosphatidyl serine-enriched lecithin, enzymatically modified lecithin, phosphatidylglycerol, phosphatidylinositol, phosphatidylethanolamine, phosphatidic acid, sphingomyelin, diphosphatidylglycerol, phosphatidylserine, phosphatidylcholine and cardiolipin; synthetic phospholipids including dimyristoylphosphatidylcholine, dimyristoylphosphatidylglycerol, distearoylphosphatidylglycerol and dipalmitoylphosphatidylcholine; and hydrogenated or partially hydrogenated lecithins and phospholipids. Non-limiting examples of synthetic phospholipid derivatives include phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), phosphatidylserine (DOPS), PEG phospholipid (mPEG-phospholipid, polyglycerin-phospholipid, functionalized-phospholipid, and terminal activated-phospholipid).

In some embodiments, the emulsifying agent comprises a surfactant, which may be ionic (anionic or cationic), zwitterionic or non-ionic, and which may be hydrophobic or hydrophilic. Examples of hydrophobic surfactants include, but are not limited to, Maisine 35-1, Imwitor 742, Capmul MCM, Capmul PG 12, Lauroglycol 90, Lauroglycol FCC, Caproyl 90, Captex 250, a fatty acid selected from the group consisting of octanoic acid, decanoic acid, undecanoic acid, lauric acid, myristic acid, palmitic acid, stearic acid, oleic acid, linoleic acid, and linolenic acid. As used herein, a hydrophobic surfactant may also be referred to as a poorly water soluble surfactant or a lipophilic surfactant.

Examples of hydrophilic surfactants may include, but are not limited to polyoxyethylene sorbitan fatty acid esters, hydrogenated castor oil ethoxylates, PEG mono- and di-esters of palmitic and stearic acids, fatty acid ethoxylates, and combinations thereof. Examples of suitable surfactants generally include, but are not limited to: polyoxyethylene-sorbitan-fatty acid esters; e.g., mono- and tri-lauryl, palmityl, stearyl and oleyl esters; e.g., products of the type known as polysorbates and commercially available under the trade name Tween®; polyoxyethylene fatty acid esters, e.g., polyoxyethylene stearic acid esters of the type known and commercially available under the trade name Myrj®; polyoxyethylene ethers, such as those available under the trade name Brij®; polyoxyethylene castor oil derivatives, e.g., products of the type known and commercially available as Cremophors®. Particularly suitable are polyoxyl 35 castor oil (Cremophor®EL) and polyoxyl 40 hydrogenated castor oil (Cremophor®RH40); a-tocopherol, a-tocopheryl polyethylene glycol succinate (vitamin E TPGS), a-tocopherol palmitate and a-tocopherol acetate; PEG glyceryl fatty acid esters such as PEG-8 glyceryl caprylate/caprate (commercially known as Labrasol®), PEG-4 glyceryl caprylate/caprate (Labrafac Hydro WL 1219), PEG-32 glyceryl laurate (Gelucire 44/14), PEG-6 glyceryl mono oleate (Labrafil® M 1944 CS), PEG-6 glyceryl linoleate (Labrafil® M 2125 CS); propylene glycol mono- and di-fatty acid esters, such as propylene glycol laurate, propylene glycol caprylate/caprate; also diethyleneglycol-monoethylether (DGME), commercially known as Transcutol® (Gattefosse, Westwood, N.J.); sorbitan fatty acid esters, such as the type known and commercially available under the name Span® (e.g., Span 85); polyoxyethylene-polyoxypropylene co-polymers, e.g., products of the type known and commercially available as Pluronic® or Poloxamer®; glycerol triacetate; and monoglycerides and acetylated monoglycerides, e.g., glycerol monodicocoate (Imwitor® 928), glycerol monocaprylate (Imwitor® 308), and mono- and di-acetylated monoglycerides.

In some embodiments, the emulsifying agent is a surfactant, a phospholipid, an amphiphilic polysaccharide, an amphiphilic protein, or a combination thereof. In some embodiments, the one or more emulsifying agents is an ionic, a zwitterionic, or a non-ionic surfactant. In some embodiments, the one or more emulsifying agents comprises Tween 20, Tween 80, Span 20, Span 40, Span 60, Span 80, lecithin, Myrj 52, Brij 35, Brij 97, a hydrocolloid gum, a modified starch, or a combination thereof.

In some embodiments, the one or more emulsifying agents comprises a combination of lecithin and Myrj 52.

The concentration of the one or more emulsifying agents present in the final nanoemulsion may vary. In some embodiments, (b)(1) comprises combining the water with one or more emulsifying agents in an amount such that the total final concentration of the emulsifying agent(s) in the nanoemulsion may be in a range of up to about 30% by weight, for example from about 0.1% to about 25%, from about 5% to about 25%, or from about 10% to about 25% by weight based on the entirety of the emulsion. In some embodiments, the resulting nanoemulsion comprises a combination of lecithin and Myrj 52 in an amount of from about 0.1% to about 25%, from about 5% to about 25%, or from about 10% to about 25% by weight based on the entirety of the emulsion.

In some embodiments, (b)(1) comprises combining the water with one or more emulsifying agents in an amount such that the total final concentration of the emulsifying agent(s) in the nanoemulsion is from about 0.1% to about 20% by weight of the oral product that contains the nanoemulsion, such as from about 1% to about 15% by weight of the oral product, such as from about 2.5% to about 10% by weight of the oral product, such as from about 5% to about 10% by weight of the oral product. In some embodiments, (b)(1) comprises combining the water with a combination of lecithin and Myrj 52 such that the total final concentration of the emulsifying agent(s) in the nanoemulsion is from about 0.1% to about 20% by weight of the nanoemulsion, such as from about 1% to about 15% by weight of the nanoemulsion, such as from about 2.5% to about 10% by weight of the nanoemulsion, such as from about 5% to about 10% by weight of the nanoemulsion.

In some embodiments, (b)(1) comprises combining the water with the one or more emulsifying agents via high shear mixing. In some embodiments, the high shear mixing is carried out for a sufficient period of time until a homogeneous mixture is formed. In some embodiments, the high shear mixing is carried out for a period of at least about 10 minutes, such as from about 10 minutes to about 60 minutes, such as from about 15 minutes to about 45 minutes, such as from about 20 minutes to about 30 minutes.

(c)

As described herein, (c) comprises combining the oil phase and the water phase to form a macroemulsion.

As referred to herein, a "macroemulsion" is an emulsion in which a dispersed phase is distributed (or "dispersed") within a continuous phase. The oil phase may be the dispersed phase, and the water phase may be the continuous phase (i.e., oil-in-water emulsion). Alternatively, the water phase may be the dispersed phase and the oil phase may be the continuous phase (i.e., water-in-oil emulsion). A macroemulsion is typically a thermodynamically unstable system with particle or droplet sizes of from about 5 nm to 200 μm. Typically, such macroemulsions may have particles with a mean radius of from 100 nm to 100 μm. A macroemulsion is generally regarded as being the name used for designating a typical or conventional emulsion that has not been processed other than to mix the continuous and dispersed phases.

In some embodiments, the macroemulsion comprises microparticles of the dispersed phase (e.g., the oil phase) in the continuous phase (e.g., the water phase). The microparticles or microdroplets may have an average size of from about 0.1 μm to about 100 μm, such as from about 1 μm to about 10 μm.

In some embodiments, (c) comprises mixing the oil phase and the water phase in order to provide the macroemulsion. In some embodiments, (c) comprises mixing the oil phase and the water phase via high shear mixing.

In some embodiments, (c) comprises mixing the oil phase and the water phase (such as via high shear mixing) for a period of at least about 10 minutes, such as at least about 15 minutes, such as at least about 20 minutes, such as at least about 30 minutes. In some embodiments, (c) comprises mixing the oil phase and the water phase (such as via high shear mixing) for a period of from about 10 minutes to about 60 minutes, such as from about 15 minutes to about 45 minutes, such as from about 20 minutes to about 30 minutes.

In some embodiments, (c) comprises combining the oil phase and the water phase (such as via mixing, such as via high shear mixing) at a temperature of no greater than about 50° C., such as at a temperature of no greater than about 45° C., such as at a temperature of no greater than about 40° C. In some embodiments, (c) comprises combining the oil phase and the water phase (such as via mixing, such as via high shear mixing) at a temperature of from about 20° C. to about 50° C., such as at a temperature of from about 25° C. to about 45° C., such as at a temperature of from about 30° C. to about 40° C.

In some embodiments, (c) comprises combining the oil phase and the water phase via high shear mixing at a temperature of no greater than about 40° C. and for a period of about 10 minutes to about 60 minutes.

In some embodiments, (c) comprises the following:
(i) first mixing the oil phase and the water phase via high shear mixing for a period of from about 1 minute to about 30 minutes; and
(ii) mixing the oil phase and the water phase for a further period of from about 10 minutes to about 60 minutes.

In some embodiments, the oil phase and the water phase are combined in (c) in a weight ratio of from about 10:1 to about 1:20. In some embodiments, the weight ratio of the oil phase to the water phase in (c) is from about 5:1 to about 1:15, such as from about 2:1 to about 1:10, such as from about 1:1 to about 1:8, such as from about 1:2 to about 1:7, such as from about 1:3 to about 1:6, such as from about 1:4 to about 1:6. In some embodiments, the weight ratio of the oil phase to the water phase in (c) is from about 1:5 to about 1:10.

(d)

As described herein, (d) comprises treating the macroemulsion to form a nanoemulsion. As referred to herein a "nanoemulsion" is a colloidal particulate system with particulates in the submicron size range. The particulates (referred to herein also as droplets or particles) are generally solid spheres, and the surfaces of such particulates are amorphous and lipophilic with a negative charge. Nanoemulsions generally comprise nanoscale particles or droplets having an average size of less than about 1,000 nm. Nanoemulsions as described herein comprise nanoparticles (or nanodroplets) of the dispersed phase emulsified in the continuous phase. In some embodiments, the nanoemulsion comprises nanoparticles of an oil phase emulsified in water or the aqueous phase.

The nanoemulsion as described herein generally comprises nanoscale particles (or nanoscale droplets) having an average size (i.e., diameter) of from about 10 nm to about 1,000 nm, for example, from about 10 nm to about 200 nm, from about 20 nm to about 100 nm, or from about 40 nm to about 100 nm. In some embodiments, the average particle size is about 100 nm, about 90 nm, about 80 nm, about 70 nm, about 60 nm, about 50 nm or about 40 nm. In some embodiments, the average particle size is from about 40 nm to about 80 nm. In some embodiments, the average particle size is from about 40 nm to about 80 nm, and the nanoemulsion is transparent.

The size of the nanoparticles may be determined by quasi-electric light scattering (QELS) as described in Bloomfield, Ann. Rev. Biophys. Bioeng., 10:421-450 (1981), incorporated herein by reference. It may also be measured by correlation spectroscopy that analyzes the fluctuation in scattering of light due to Brownian motion, or by transmission electron microscopy (TEM).

The nanoemulsion may be prepared in (d) using a high-energy method or a low-energy method. High-energy methods utilize mechanical devices (homogenizers) that are capable of generating intense disruptive forces that are capable of disrupting the oil and aqueous phases into tiny oil droplets (see McClements and Rao, Critical Reviews in Food Science and Nutrition, 51, 285-330 (2011)). Such high-energy approaches include the use of high pressure valve homogenizers, microfluidizers, and sonication methods. Low-energy approaches may rely on the spontaneous formation of tiny oil droplets within systems when the solution or environmental conditions are altered.

For example, nanoemulsions as disclosed herein can be prepared by mechanical processes which employ shear force to break large emulsion droplets into smaller ones, such as high-pressure homogenization (HPH, including microfluidization), high-amplitude ultrasonic processing, and ultrasound-assisted emulsification. In some embodiments, the nanoemulsion may be formed via the use of a high pressure valve homogenizer, a microfluidizer, or an ultrasonic homogenizer (including ultrasonic jet homogenizers and ultrasonic probe homogenizers).

In some embodiments, (d) comprises treating the macroemulsion in a homogenizer to form the nanoemulsion. The homogenizer may be selected from a high pressure valve homogenizer, an ultrasonic jet homogenizer, an ultrasonic probe homogenizer or mixtures thereof.

In some embodiments, (d) comprises sonicating the macroemulsion. The macroemulsion may be sonicated in an ultrasonic jet homogenizer or an ultrasonic probe homogenizer.

In some embodiments, (d) comprises treating the macroemulsion in a microfluidizer to form the emulsion.

The aqueous and oil phases may thus be combined and homogenized with, for example, a probe sonicator (Sonics and Materials, USA), a high pressure homogenizer (such as one made by Gauline or Avestine, or the like), or a microfluidizer, to obtain the desired nanoemulsion. The number of passes through a high pressure homogenizer/microfluidizer may vary, depending on the desired particle size for the nanoemulsions. A variety of methods are known in the art for producing nanoemulsions comprising nano-sized particles of particular size ranges, using for example, sonication or homogenization. One such method is described in U.S. Pat. No. 4,737,323, incorporated herein by reference.

In some embodiments, the macroemulsion is treated using a homogenizer, such as an ultrasonic jet or probe homogenizer, and by passing the macroemulsion through the homogenizer at a flow rate of from about 50 mL/min to about 9 L/min. In some embodiments, the macroemulsion is passed through the homogenizer at a flow rate of from about 100 mL/min to about 1000 mL/min, or about 100 mL/min to about 500 mL/min, such as from about 150 mL/min to about 250 mL/min.

In some embodiments, the macroemulsion is sonicated (e.g., by an ultrasonic jet or probe homogenizer) at an amplitude of from about 1 µm to about 100 µm, such as from about 50 µm to about 90 µm, such as from about 75 µm to about 85 µm.

In some embodiments, the macroemulsion is treated (e.g., using a homogenizer, such as an ultrasonic jet or probe homogenizer) at a temperature of no greater than about 50° C. In some embodiments, the macroemulsion is treated (e.g., using a homogenizer, such as an ultrasonic jet or probe homogenizer) at a temperature of from about 20° C. to about 50° C., such as from about 20° C. to about 40° C., such as from about 25° C. to about 35° C. In some embodiments, the macroemulsion is passed through the homogenizer (e.g., an ultrasonic jet or probe homogenizer) at the above-noted temperature ranges.

In some embodiments, the resulting nanoemulsion may be passed through a filter in order to remove any particles or droplets of the dispersed phase that are not in the nanoparticle range. As described above, the nanoemulsion as described herein generally comprises nanoscale particles having an average size of from about 10 nm to about 1,000 nm. Therefore, in some embodiments, (d) comprises passing the resultant nanoemulsion through a filter system in order to provide a final nanoemulsion that comprises a dispersed having an average particle size of from about 10 nm to about 1,000 nm. The filter system may have an aperture size of no greater than about 1,000 nm in order to provide the desired particle size distribution in the nanoemulsion. In some embodiments, the filter system has an aperture size of no greater than about 500 nm in order to provide a nanoemulsion having a dispersed phase with an average particle size of from about 10 nm to about 500 nm.

Total Process

In some embodiments, the process further comprises adding one or more additives to the nanoemulsion. The additive(s) may be combined with the oil in the oil phase. Alternatively or in addition, the additive(s) may be combined with the water in the water phase. Alternatively or in addition, the additive(s) may be combined with the resulting mixture after (c); in other words, the additive(s) may be added to the macroemulsion. Alternatively or in addition, the additive(s) may be combined with the resulting mixture after (d); in other words, the additive(s) may be added to the nanoemulsion itself.

The one or more additive(s) may be selected from the group consisting of a flavoring agent (or "flavorant"), a taste modifier, a preservative, a humectant, a sweetener, a binder, a buffering agent, salt, and mixtures thereof.

Flavoring Agent and Taste Modifier

In some embodiments, the process further comprises adding a flavorant to the oil phase, the water phase and/or to both phases in the macroemulsion or nanoemulsion. As used herein, the terms "flavor" and "flavorant" refer to materials which, where local regulations permit, may be used to create a desired taste, aroma or other somatosensory sensation in a product for adult consumers. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy.

They may include naturally occurring flavor materials, botanicals, extracts of botanicals, synthetically obtained materials, or combinations thereof (e.g., tobacco, *cannabis*, licorice (liquorice), *hydrangea*, eugenol, Japanese white bark *magnolia* leaf, chamomile, fenugreek, clove, maple, matcha, menthol, Japanese mint, aniseed (anise), cinnamon, turmeric, Indian spices, Asian spices, herb, wintergreen, cherry, berry, red berry, cranberry, peach, apple, orange, mango, clementine, lemon, lime, tropical fruit, *papaya*, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, *betel*, shisha, pine, honey essence, rose oil, vanilla, lemon oil, orange oil, orange blossom, cherry blossom, *cassia*, caraway, cognac, jasmine, ylang-ylang, sage, fennel, wasabi, piment, ginger, coriander, coffee, hemp, a mint oil from any species of the genus Mentha, *eucalyptus*, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, *curcuma*, cilantro, myrtle, cassis, valerian, pimento, mace, damien, marjoram, olive, lemon balm, lemon basil, chive, *carvi, verbena*, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, liquid such as an oil, solid such as a powder, or gas. In some embodiments, the flavor comprises menthol, spearmint and/or peppermint. In some embodiments, the flavor comprises flavor components of cucumber, blueberry, citrus fruits and/or redberry. In some embodiments, the flavor comprises eugenol. In some embodiments, the flavor comprises flavor components extracted from tobacco. In some embodiments, the flavor comprises flavor components extracted from *cannabis*.

In some embodiments, the flavor may comprise a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to eucolyptol, WS-3.

In some embodiments, the flavorant is lipophilic. Without wishing to be bound by theory, formulation of a lipophilic flavorant as an emulsion may enhance the stability of the flavorant (e.g., toward oxidation or evaporation). In some embodiments, the flavorant is susceptible to oxidation, meaning exposure to air results in the degradation of components in the flavorant due to chemical changes. Examples of functional groups which may be present in flavorant components exhibiting susceptibility to oxidation include, but are not limited to, alkenes, aldehydes, and/or ketones. In some embodiments, the flavorant comprises a citrus oil. Citrus oils contain, for example, terpene components which may be susceptible to oxidation, evaporation, or both and, thus, may particularly benefit from inclusion within a product in the form of an emulsion as provided herein.

In some embodiments, the flavoring agent may comprise a terpene. In some embodiments, the terpene is a terpene derivable from a phytocannabinoid producing plant, such as a plant from the stain of the *Cannabis sativa* species, such as hemp. Suitable terpenes in this regard include so-called "C10" terpenes, which are those terpenes comprising 10 carbon atoms, and so-called "C15" terpenes, which are those terpenes comprising 15 carbon atoms. In some embodiments, the nanoemulsion or oral product containing the nanoemulsion comprises more than one terpene. For example, the nanoemulsion or oral product containing the nanoemulsion may comprise one, two, three, four, five, six, seven, eight, nine, ten or more terpenes as defined herein. In some embodiments, the terpene is selected from pinene (alpha and beta), geraniol, linalool, limonene, carvone, eucalyptol, menthone, iso-menthone, piperitone, myrcene, beta-bourbonene, germacrene and mixtures thereof.

The amount of flavorant utilized in the emulsion can vary, but is typically up to about 10% by weight, and certain embodiments are characterized by a flavoring agent content of at least about 0.1% by weight, such as about 0.5% to about 10% by weight, about 1 to about 6% by weight, or about 2% to about 5% by weight, based on the total weight of the emulsion.

In some embodiments, the process further comprises adding a taste modifier to the oil phase, the water phase and/or to both phases in the macroemulsion or nanoemulsion. In some embodiments, the taste modifier may mask the bitterness of the cannabinoid in the emulsion. The taste modifying agent may improve the organoleptic properties of a nanoemulsion as disclosed herein, and may serve to mask, alter, block, or improve e.g., the flavor of a composition as described herein. Non-limiting examples of such taste modifiers include analgesic or anesthetic herbs, spices, and flavors which produce a perceived cooling (e.g., menthol, *eucalyptus*, mint), warming (e.g., cinnamon), or painful (e.g., capsaicin) sensation. Certain taste modifiers fall into more than one overlapping category.

In some embodiments, the taste modifier modifies one or more of bitter, sweet, salty, or sour tastes. In some embodiments, the taste modifier targets pain receptors. In some embodiments, the cannabinoid has a bitter taste, and the oral product comprises a taste modifier which masks or blocks the perception of the bitter taste. In some embodiments, the taste modifier is a substance which targets pain receptors (e.g., vanilloid receptors) in the user's mouth to mask e.g., a bitter taste of another component (e.g., the cannabinoid). In some embodiments, the taste modifier is capsaicin.

In some embodiments, the taste modifier is the amino acid gamma-amino butyric acid (GABA), referenced herein above with respect to amino acids. Studies in mice suggest that GABA may serve function(s) in taste buds in addition to synaptic inhibition. See, e.g., Dvoryanchikov et al., J Neurosci. 2011 Apr. 13; 31(15):5782-91. Without wishing to be bound by theory, GABA may suppress the perception of certain tastes, such as bitterness. In some embodiments, the composition comprises caffeine and GABA.

In some embodiments, the taste modifier is adenosine monophosphate (AMP). AMP is a naturally occurring nucleotide substance which can block bitter food flavors or enhance sweetness. It does not directly alter the bitter flavor, but may alter human perception of "bitter" by blocking the associated receptor.

In some embodiments, the taste modifier is lactisole. Lactisole is an antagonist of sweet taste receptors. Temporarily blocking sweetness receptors may accentuate e.g., savory notes.

When present, a representative amount of taste modifier is about 0.01% by weight or more, about 0.1% by weight or more, or about 1.0% by weight or more, but will typically make up less than about 10% by weight of the total weight of the nanoemulsion, (e.g., from about 0.01%, about 0.05%, about 0.1%, or about 0.5%, to about 1%, about 5%, or about 10% by weight of the total weight of the nanoemulsion).

In some embodiments, the taste modifier selected from the group consisting of an analgesic or anesthetic herb, spice, or flavor which produces a perceived cooling or warming effect, gamma-aminobutyric acid, capsaicin, and adenosine monophosphate. In some embodiments, the taste sensation modified by the taste modifier is bitterness, sweetness, saltiness, or sourness. In some embodiments, the taste sensation is bitterness. In some embodiments, the taste modifier is capsaicin.

Humectant

In some embodiments, the process further comprises adding a humectant to the oil phase, the water phase and/or to both phases in the macroemulsion or nanoemulsion. One or more humectants may be employed in the emulsion of the present disclosure. The humectant may be present in the water phase and/or the oil phase of the emulsion.

Examples of humectants include, but are not limited to, glycerin, 1,2-propanediol (propylene glycol), 1,3-propanediol, dipropylene glycol, sorbitol, xylitol, mannitol, and the like. In some embodiments, the humectant is or comprises glycerin. In some embodiments, the oral product comprises glycerin. In some embodiments, the emulsion comprises glycerine. In some embodiments, the humectant is or comprises propylene glycol. In some embodiments, the oral product comprises propylene glycol. In some embodiments, the emulsion comprises propylene glycol.

Where included, the humectant is typically provided in an amount sufficient to provide desired moisture attributes to the composition. Further, in some instances, the humectant may impart desirable flow characteristics to the composition for depositing in a mold.

When present in the emulsion, the humectant (such as glycerin and/or propylene glycol) may be present in an amount of from about 0.1% to about 40% by weight of the emulsion, such as from about 1% to about 35% by weight of the emulsion, such as from about 5% to about 30% by weight of the emulsion, such as from about 10% to about 30% by weight of the emulsion, such as from about 15% to about 30% by weight of the emulsion, such as from about 20% to about 25% by weight of the emulsion.

Sweetener

In some embodiments, the process further comprises adding a sweetener to the oil phase, the water phase and/or to both phases in the macroemulsion or nanoemulsion. In order to improve the sensory properties of the emulsion or the oral product comprising the emulsion according to the disclosure, one or more sweeteners may be added. The sweeteners can be any sweetener or combination of sweeteners, in natural or artificial form, or as a combination of natural and artificial sweeteners. Examples of natural sweeteners include fructose, sucrose, glucose, maltose, isomaltulose, mannose, galactose, lactose, *stevia*, honey, and the like. Examples of artificial sweeteners include sucralose, maltodextrin, saccharin, aspartame, acesulfame K, neotame and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates).

In some embodiments, the sweetener is selected from the group consisting of fructose, sucrose, glucose, maltose, mannose, galactose, lactose, *stevia*, honey, sucralose, isomaltulose, maltodextrin, saccharin, aspartame, acesulfame K, neotame, erythritol, arabitol, ribitol, isomalt, maltitol, dulcitol, iditol, mannitol, xylitol, lactitol, sorbitol, and mixtures thereof. In some embodiments, the sweetener is selected from the group consisting of sucralose, acesulfame K, aspartame, maltodextrin, mannitol, sucrose, and mixtures thereof. In some embodiments, the sweetener may be sucralose and/or acesulfame K.

When present in the emulsion, the sweetener (such as sucralose and/or acesulfame K) may be present in an amount of from about 0.01% to about 10% by weight of the emulsion, such as from about 0.1% to about 5% by weight of the emulsion, such as from about 0.5% to about 2.5% by weight of the emulsion, such as from about 1% to about 2.5% by weight of the emulsion.

Binder

In some embodiments, the process further comprises adding a binder to the oil phase, the water phase and/or to both phases in the macroemulsion or nanoemulsion. A binder (or combination of binders) may be employed in certain embodiments, in amounts sufficient to provide the desired physical attributes and physical integrity to the composition, and binders also often function as thickening or gelling agents. Typical binders can be organic or inorganic, or a combination thereof. Representative binders include cellulose derivatives (e.g., cellulose ethers), povidone, sodium alginate, starch-based binders, pectin, gums, carrageenan, pullulan, zein, and the like, and combinations thereof. In some embodiments, the binder comprises pectin or carrageenan or combinations thereof.

The amount of binder utilized in the composition can vary, but is typically up to about 30% by weight, and certain embodiments are characterized by a binder content of at least about 0.1% by weight, such as from about 1% to about 30% by weight, or about 1% to about 10% by weight, based on the total weight of the nanoemulsion.

In some embodiments, the binder comprises a cellulose derivative. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). In some embodiments, the cellulose derivative is one or more of methylcellulose, HPC, HPMC, hydroxyethyl cellulose, and CMC. In some embodiments, the cellulose derivative is HPC. In some embodiments, the cellulose derivative is a combination of HPC and HPMC. In some embodiments, the nanoemulsion comprises from about 1% to about 10% of the cellulose derivative by weight, based on the total weight of the nanoemulsion, with certain embodiments comprising from about 1% to about 5% by weight of cellulose derivative, based on the weight of the nanoemulsion.

In certain embodiments, the binder includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by weight, for example, from about 0.1, about 0.2, about 0.3, about 0.4, about 0.5, about 0.6, about 0.7, about 0.8, about 0.9, or about 1%, to about 2, about 3, about 4, or about 5% by weight, based on the total weight of the nanoemulsion.

Buffering Agent

In some embodiments, the process further comprises adding a buffering agent to the oil phase, the water phase and/or to both phases in the macroemulsion or nanoemulsion. Indeed, in certain embodiments, the emulsion or the oral product comprising the emulsion of the present disclosure can comprise pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. Where present, the buffering agent is typically present in an amount less than about 5% based on the weight of the emulsion or the oral product comprising the emulsion; for example, from about 0.5% to about 5%, such as, e.g., from about 0.75% to about 4%, from about 0.75% to about 3%, or from about 1% to about 2% by weight, based on the total weight of the emulsion or the oral product comprising the emulsion.

Non-limiting examples of suitable buffers include alkali metals acetates, glycinates, phosphates, glycerophosphates, citrates, carbonates, hydrogen carbonates, borates, or mixtures thereof. In some embodiments, the buffering agent is selected from the group consisting of sodium carbonate, sodium bicarbonate, sodium phosphate, ammonium phosphate, and mixtures thereof.

The oral product according to the disclosure may have any suitable pH. In certain embodiments, the oral product of the present disclosure has a pH of from about 4 to about 7. In certain embodiments, the oral product of the present disclosure has a pH of from about 4 to about 6.5. In certain embodiments, the oral product of the present disclosure has a pH of from about 4.5 to about 7. In certain embodiments, the oral product of the present disclosure has a pH of from about 4.5 to about 6.5. In certain embodiments, the oral product of the present disclosure has a pH of from about 4 to about 6.5. In certain embodiments, the oral product of the present disclosure has a pH of from about 4.5 to about 6. In certain embodiments, the oral product of the present disclosure has a pH of from about 5 to about 6.

The pH of the oral product may be measured by any suitable technique. For example, the pH of the oral product may be measured by contacting 5 grams of oral product with 95 g of water (100 g total) and then mixing for 5 minutes. After mixing the pH of the solution may be measured with a pH probe.

The nanoemulsion according to the disclosure may have any suitable pH. In certain embodiments, the nanoemulsion of the present disclosure has a pH of from about 4 to about 7. In certain embodiments, the nanoemulsion of the present disclosure has a pH of from about 4.5 to about 7. In certain embodiments, the nanoemulsion of the present disclosure has a pH of from about 5 to about 7. In certain embodiments, the nanoemulsion of the present disclosure has a pH of from about 5.5 to about 7. In certain embodiments, the nanoemulsion of the present disclosure has a pH of from about 6 to about 7. In certain embodiments, the nanoemulsion of the present disclosure has a pH of from about 6 to about 6.5.

Salt

In some embodiments, the emulsion or the oral product comprising the emulsion according to the disclosure comprises a salt (e.g., an alkali metal salt), typically employed in an amount sufficient to provide desired sensory attributes to the product. Non-limiting examples of suitable salts include sodium chloride, potassium chloride, ammonium chloride, flour salt, sodium acetate, sodium citrate, and the like. When present, a representative amount of salt is at least about 0.5% by weight, such as at least about 1% by weight, such as at least about 1.5% by weight. In some embodiments, the emulsion may comprise salt in an amount of from about 0.5% to about 10% by weight, such as from about 1% to about 7.5% by weight, such as from about 1.5% to about 5% by weight, based on the total weight of the emulsion.

Stabilizer

In some embodiments, the nanoemulsion may further comprise a stabilizer to assist in maintaining the nanoemulsion. Representative examples of suitable types of stabilizers include polysaccharides, polyols, sorbitan esters, glycerol esters, polyethylene glycol esters, block polymers, acrylic polymers (such as Pemulen), silicon based surfactants, and polysorbates. In some embodiments, the stabilizer is sodium oleate, glycerine, xylitol, sorbitol, ascorbic acid, sodium edetate, a sorbitan ester, a glycerol monoester, or a combination thereof.

The concentration of the stabilizer present in the emulsion may vary. When present, the concentration of the stabilizer may be in a range of up to about 10% by weight, for example from about 0.01% to about 10%, from about 0.1% to about 5%, or from about 0.5% to about 1% by weight based on the weight of the emulsion.

Other Additives

In some embodiments, the process further comprises adding other additives to the oil phase, the water phase and/or to both phases in the macroemulsion or nanoemulsion. For example, in some embodiments, the process further comprises adding a preservative to the oil phase, the water phase and/or to both phases in the macroemulsion or nanoemulsion.

For example, the emulsion or the oral product comprising the emulsion can be processed, blended, formulated, combined, and/or mixed with other materials or ingredients. The additives can be artificial, or can be obtained or derived from herbal or biological sources. Examples of further types of additives include thickening or gelling agents (e.g., fish gelatin), preservatives (e.g., potassium sorbate, sodium benzoate, calcium propionate, and the like), disintegration aids, zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof. See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., US Pat. App. Pub. No. 2010/0291245 to Gao et al., and US Pat. App. Pub. No. 2007/0062549 to Holton, Jr. et al., each of which is incorporated herein by reference. Typical inclusion ranges for such additional additives can vary depending on the nature and function of the additive and the intended effect on the final composition, with an example range of up to about 10% by weight, (e.g., from about 0.1% to about 5% by weight) based on total weight of the emulsion.

For example, where present, a preservative (such as potassium sorbate, sodium benzoate, calcium propionate, or the like) can be included in the emulsion in an amount of from about 0.01% to about 5% by weight of the emulsion, such as from about 0.05% to about 2.5% by weight of the emulsion, such as from about 0.1% to about 1% by weight of the emulsion.

A colorant may be employed in amounts sufficient to provide the desired physical attributes to the emulsion or the oral product comprising the emulsion according to the present disclosure. Examples of colorants include various dyes and pigments, such as caramel coloring and titanium dioxide. The amount of colorant utilized in the emulsion or the oral product comprising the emulsion can vary, but when present is typically up to about 3% by weight, such as from about 0.1%, about 0.5%, or about 1%, to about 3% by weight, based on the total weight of the emulsion.

The aforementioned additives can be employed together (e.g., as additive formulations) or separately (e.g., individual additive components can be added at different stages involved in the preparation of the final product). Furthermore, the aforementioned types of additives may be encapsulated as provided in the final product or composition.

Exemplary encapsulated additives are described, for example, in WO2010/132444 to Atchley, which is incorporated herein by reference.

Nanoemulsion

In accordance with some embodiments described herein, there is provided a nanoemulsion comprising at least one cannabinoid, wherein the nanoemulsion is obtained or obtainable by a process comprising:

(a) providing an oil phase containing at least one cannabinoid;

(b) providing a water phase;

(c) combining the oil phase and water phase to form a macroemulsion; and (d) treating the macroemulsion to form a nanoemulsion; wherein at least one of the oil phase and the water phase comprises one or more emulsifying agents.

The nanoemulsion may be obtained or obtainable by the process as described in detail hereinabove.

The nanoemulsion as described herein may be characterized by reference to a polydispersity index. Polydispersity indicates the uniformity of droplet size in a nanoemulsion. The higher the value of polydispersity, the lower will be the uniformity of droplet size. It may be defined as the ratio of standard deviation to mean droplet size. It may be measured by spectrophotometric methods. In some embodiments, it may be advantageous to provide nanoemulsions with a low polydispersity index, e.g., less than about 0.5. In some embodiments, the nanoemulsion has a polydispersity index of less than about 0.3.

The nanoemulsion as described herein generally comprises nanoscale particles having an average size of from about 10 nm to about 1,000 nm, for example, from about 10 nm to about 200 nm, from about 20 nm to about 100 nm, or from about 40 nm to about 100 nm. In some embodiments, the average particle size is about 100 nm, about 90 nm, about 80 nm, about 70 nm, about 60 nm, about 50 nm or about 40 nm. In some embodiments, the average particle size is from about 40 nm to about 80 nm. In some embodiments, the average particle size is from about 40 nm to about 80 nm, and the nanoemulsion is transparent.

In some embodiments, the nanoemulsion comprises nanoparticles or nanodroplets of oil phase dispersed in the water phase. In some embodiments, the nanodoplets have an average diameter (or average size) of from about 1 nm to about 500 nm, such as from about 1 nm to about 200 nm, such as from about 10 nm to about 200 nm.

The nanoemulsion as described herein may be characterized by reference to zeta potential. Zeta potential is a measure of the charge on the surface of a droplet in the emulsion (or nanoemulsion). In some embodiments, the zeta potential of the nanoparticles is less than about −10 mV. In some embodiments, the zeta potential of the nanoparticles is less than about −20 mV. In some embodiments, the zeta potential of the nanoparticles is less than about −30 mV. In some embodiments, the zeta potential of the nanoparticles is less than about −40 mV. In some embodiments, the zeta potential of the nanoparticles is less than about −50 mV. In some embodiments, the zeta potential of the nanoparticles is from about −100 mV to about −10 mV, such as from about −100 mV to about −20 mV, such as from about −100 mV to about −30 mV, such as from about −100 mV to about −40 mV, such as from about −100 mV to about −50 mV. As appreciated by one skilled in the art, zeta potential is the measure of the electrical charge on particle surface in colloidal dispersions. Zeta potential may be measured with a zeta analyser, for example a Malvern Zetasizer.

As described herein, the nanoemulsion comprises an oil phase and a water phase. The emulsion further comprises at least one cannabinoid contained in the oil phase.

The nanoemulsion may comprise an oil phase as the continuous phase or the dispersed phase. The nanoemulsion may comprise a water phase as the continuous phase or the dispersed phase. In some embodiments, the nanoemulsion comprises an oil phase as the continuous phase and an aqueous phase as the dispersed phase (i.e., a water-in-oil emulsion). In some embodiments, the nanoemulsion comprises an aqueous phase as the continuous phase and an oil phase as the dispersed phase (i.e., an oil-in-water emulsion). In some embodiments, the nanoemulsion may be a water-in-oil-in-water emulsion. In some embodiments, the emulsion may be an oil-in-water-in-oil emulsion.

In some embodiments, the emulsion is an oil-in-water emulsion, and the cannabinoid is present in the dispersed oil phase. In some embodiments, the emulsion is a water-in-oil emulsion, and the cannabinoid is present in the continuous oil phase.

In some embodiments, the emulsion is a nanoemulsion comprising nanoparticles of the oil phase dispersed in the aqueous phase. In some embodiments, the cannabinoid is present within the nanoparticles of the oil phase in the nanoemulsion.

In some embodiments, the cannabinoid (such as cannabidiol) is present in the nanoemulsion in a concentration of at least about 0.001% by weight of the emulsion, such as in a range from about 0.001% to about 30% by weight of the emulsion. In some embodiments, the cannabinoid (such as cannabidiol) is present in a concentration from about 0.1% to about 20% by weight, based on the total weight of the emulsion. In some embodiments, the cannabinoid (such as cannabidiol) is present in a concentration from about 0.1% to about 10% by weight, such as from about 0.5% to about 10%, such as from about 1% to about 10%, such as from about 1% to about 5% by weight, based on the total weight of the emulsion. In some embodiments, the cannabinoid (such as cannabidiol) is present in a concentration from about 2.5% to about 15% by weight, such as from about 5% to about 15%, such as from about 5% to about 10%, based on the total weight of the emulsion.

In some embodiments, the weight ratio of oil to cannabinoid (such as cannabidiol) in the nanoemulsion is from about 10:1 to about 1:10, such as from about 5:1 to about 1:5, such as from about 3:1 to about 1:3, such as from about 3:1 to about 1:1, such as from about 2:1 to about 1:1.

In some embodiments, the weight ratio of water to cannabinoid (cannabidiol) in the nanoemulsion is from about 20:1 to about 1:10, such as from about 15:1 to about 1:1, such as from about 10:1 to about 1:1, such as from about 8:1 to about 5:1.

For the avoidance of doubt, combinations of the above end points are explicitly envisaged by the present disclosure. This applies to any of the ranges disclosed herein.

In accordance with some embodiments described herein, there is provided a nanoemulsion comprising:

(a) an oil phase containing at least one cannabinoid;

(b) a water phase;

wherein at least one of the oil phase and the water phase comprises one or more emulsifying agents; and wherein the zeta potential of the nanoemulsion is less than about −10 mV.

The nanoemulsion may be obtained or obtainable by the process as described in detail hereinabove. The nanoemulsion may have any of the features as described hereinabove.

Oral Product

In accordance with some embodiments described herein, there is provided an oral product containing a nanoemulsion comprising at least one cannabinoid, wherein the nanoemulsion:

(a) is obtained or obtainable by a process as defined herein; or (b) comprises:
(i) an oil phase containing at least one cannabinoid;
(ii) a water phase;
wherein at least one of the oil phase and the water phase comprises one or more emulsifying agents; and
wherein the zeta potential of the nanoemulsion is less than about −10 mV.

The oral product is configured for oral use, and thus for insertion into the user's mouth (i.e., oral cavity).

The amount of the nanoemulsion in the oral product may vary and may be any suitable amount for forming a product suitable for oral application. In some embodiments, the nanoemulsion is present in the oral product in an amount of from about 1% to about 75% by weight of the oral product, such as from about 5% to about 60% by weight of the oral product, such as from about 10% to about 50% by weight of the oral product, such as from about 15% to about 45% by weight of the oral product, such as from about 20% to about 40% by weight of the oral product, such as from about 25% to about 40% by weight of the oral product, such as from about 30% to about 40% by weight of the oral product.

In some embodiments, the nanoemulsion is present in the oral product in an amount of from about 20% to about 40% by weight of the oral product.

In some embodiments, the cannabinoid (such as cannabidiol) is thus present in the oral product in a concentration of at least about 0.001% by weight of the oral product, such as in a range from about 0.001% to about 20% by weight of the oral product. In some embodiments, the cannabinoid is present in the oral product in a concentration of from about 0.1% to about 15% by weight, based on the total weight of the oral product. In some embodiments, the cannabinoid (such as cannabidiol) is present in a concentration from about 1% to about 15% by weight, such as from about 5% to about 15% by weight, based on the total weight of the oral product. In some embodiments, the cannabinoid (such as cannabidiol) is present in the oral product in a concentration of from about 0.5% to about 10% by weight, such as from about 1% to about 7.5% by weight, such as from 1.5% to about 5% by weight, such as from about 1.5% to about 2.5% by weight, based on the total weight of the oral product.

In some embodiments, the oral product further comprises a filler in combination with the nanoemulsion. The emulsion as disclosed herein may be associated with a filler in various ways (i.e., in an oral product comprising an emulsion as disclosed herein). For example, the emulsion may be disposed on the surface of a filler, may be dispersed in or impregnated into (e.g., adsorbed or absorbed) a filler, or a filler and the emulsion may be present in an oral product without being physically combined or in physical contact (e.g., they may be provided separately and independently within the same product).

Fillers may fulfil multiple functions, such as enhancing certain organoleptic properties such as texture and mouthfeel, enhancing cohesiveness or compressibility of the product, and the like, depending on the product and the association between the filler and the emulsion. In some embodiments, the filler is a porous particulate material and is cellulose-based. For example, the filler may be a non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof.

In some embodiments, the filler is a cellulose material selected from the group consisting of maize fiber, oat fiber, barley fiber, rye fiber, buckwheat fiber, sugar beet fiber, bran fiber, bamboo fiber, wood pulp fiber, cotton fiber, citrus pulp fiber, grass fiber, willow fiber, poplar fiber, cocoa fiber, derivatives thereof, and combinations thereof. In some embodiments, the filler is a cellulose material selected from the group consisting of maize fiber, oat fiber, sugar beet fiber, bamboo fiber, wood pulp fiber, cotton fiber, grass fiber, derivatives thereof, and combinations thereof. In some embodiments, the filler is a cellulose material selected from the group consisting of sugar beet fiber, wood pulp fiber, bamboo fiber, derivatives thereof, and combinations thereof.

In some embodiments, the filler is derived from any of maize fiber, oat fiber, barley fiber, rye fiber, buckwheat fiber, sugar beet fiber, bran fiber, bamboo fiber, wood pulp fiber, cotton fiber, citrus pulp fiber, grass fiber, willow fiber, poplar fiber, cocoa fiber, or combinations thereof. In some embodiments, the filler is derived from wood pulp fiber.

In some embodiments, the filler is a cellulose material. One particularly suitable filler for use in the compositions described herein is microcrystalline cellulose ("MCC"). MCC is typically derived from wood pulp fiber. MCC is composed of glucose units connected by a 1-4 beta glycosidic bond, and may be synthesized by partially depolymerizing alpha-cellulose, by, for example, reactive extrusion, enzyme mediated depolymerisation, mechanical grinding, ultrasonication, steam explosion and/or acid hydrolysis. The MCC may be synthetic or semi-synthetic, or it may be obtained entirely from natural celluloses. The MCC may be selected from the group consisting of AVICEL® grades PH-100, PH-101, PH-102, PH-103, PH-105, PH-112, PH-113, PH-200, PH-300, PH-301, PH-302, VIVACEL® grades 101, 102, 12, 20 and EMOCEL® grades 50M and 90M, and the like, and mixtures thereof. In some embodiments, the oral product comprises MCC as the filler.

In some embodiments, the filler is a non-tobacco plant material or a derivative thereof. Non-limiting examples of derivatives of non-tobacco plant material include starches (e.g., from potato, wheat, rice, corn), natural cellulose, and modified cellulosic materials. Additional examples of potential fillers include maltodextrin, dextrose, calcium carbonate, calcium phosphate, lactose, mannitol, xylitol, and sorbitol. Combinations of fillers can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the composition based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, *canna*, chestnuts, colacasia, katakuri, kudzu, malanga, millet, oats, oca, Polynesian arrowroot, sago, sorghum, sweet potato, *quinoa*, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "genetically modified" starches. Other starches are obtained and subsequently modified by chemical, enzymatic, or physical means. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, acetylation, hydroxypropylation, and/or partial hydrolysis. Enzymatic treatment includes subjecting native starches to enzyme isolates or concentrates, microbial enzymes, and/or enzymes native to plant materials, e.g., amylase present in corn kernels to modify corn starch. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, and starch sodium octenyl succinate.

The amount of filler can vary, but when present, is typically at least about 50 percent by weight of the oral product comprising the emulsion, based on the total weight of the oral product. A typical range of filler (e.g., MCC) within the composition can be from about 10 to about 75 percent by total weight of the oral product. For example, the filler (e.g., MCC) may be present in the oral product in an amount of at least about 50% by weight of the oral product, such as at least about 55% by weight of the oral product, such as at least about 60% by weight of the oral product. In some embodiments, the filler (e.g., MCC) may be present in the oral product in an amount of from about 50% to about 99% by weight of the oral product, such as from about 50% to about 95% by weight of the oral product, such as from about 50% to about 90% by weight of the oral product, such as from about 55% to about 85% by weight of the oral product, such as from about 60% to about 80% by weight of the oral product, such as from about 60% to about 75% by weight of the oral product.

In some embodiments, the oral product comprises microcrystalline cellulose in an amount of from about 55% to about 95% by weight of the oral product. In some embodiments, the oral product comprises microcrystalline cellulose in an amount of from about 55% to about 80% by weight of the oral product.

In some embodiments, the weight ratio of the filler (such as microcrystalline cellulose) to the nanoemulsion may be from about 10:1 to about 1:10, such as from about 5:1 to about 1:5, such as from about 5:1 to about 1:2, such as from about 3:1 to about 1:1, such as from about 2:1 to about 1:1.

In some embodiments, the weight ratio of filler (such as microcrystalline cellulose) to cannabinoid is from about 5:1 to about 100:1, such as from about 10:1 to about 60:1, such as from about 15:1 to about 50:1, such as from about 20:1 to about 40:1, such as from about 25:1 to about 35:1. In some embodiments, the weight ratio of microcrystalline cellulose to cannabidiol is from about 5:1 to about 100:1, such as from about 10:1 to about 60:1, such as from about 15:1 to about 50:1, such as from about 20:1 to about 40:1, such as from about 25:1 to about 35:1.

In some embodiments, the oral product comprises water. In some embodiments, the water content of the oral product is at least about 10% by weight of the oral product. In some embodiments, the water content is less than about 30% by weight of the oral product. As referred to herein, "the water content" means the total amount of water in the oral product, as included in any form. Water may be present as, for example, purified or ultrapure water, saline, buffered saline, or a buffered aqueous phase.

In some embodiments, the only water present in the composition is contained within an emulsion in the product.

In some embodiments, the oral product has a water content of from about 10% to about 30% by weight of the oral product, such as from about 10% to about 25% by weight of the oral product, such as from about 10% to about 20% by weight of the oral product, such as from about 11% to about 15% by weight of the oral product. In some embodiments, the oral product has a water content of from about 12% to about 30% by weight of the oral product, such as from about 13% to about 25% by weight of the oral product, such as from about 14% to about 25% by weight of the oral product, such as from about 15% to about 20% by weight of the oral product.

In some embodiments, the weight ratio of filler to water is from about 1:1 to about 20:1, such as from about 1:1 to about 10:1, such as from about 2:1 to about 5:1, such as from about 3:1 to about 5:1.

Configured for Oral Use

In some embodiments, the oral product may be a solid oral product. By "solid" is meant compositions which can substantially sustain their physical shape when unsupported by external means, e.g., packaging etc. Thus, they are considered to be solid, solid like, in solid form or in solid-like form at room temperature. For the avoidance of doubt the solid product must remain substantially solid at up to 30° C.

By solid-like, it is understood that some materials are considered on a day to day basis to be solid, yet over an extremely long period of time, may alter in shape, e.g., amorphous materials such as glass etc. However, they are considered to be solid-like as, for the purpose they fulfil, they are solid.

The emulsion and compositions and products comprising the emulsion as described herein are configured for oral use. The term "configured for oral use" as used herein means that the product is provided in a form such that during use, saliva in the mouth of the user causes one or more of the components of the emulsion, composition, or product (e.g., flavoring agents and/or active ingredients) to pass into the mouth of the user. In certain embodiments, the emulsion, composition, or product is adapted to deliver components to a user through mucous membranes in the user's mouth, the user's digestive system, or both, and, in some instances, said component is an active ingredient that can be absorbed through the mucous membranes in the mouth or absorbed through the digestive tract when the product is used.

Products configured for oral use as described herein (into which the disclosed emulsion are incorporated) are in a solid form. The products may take various forms, including pastilles, gums, lozenges, tablets, and powders. The products may be provided in pouch form in which a solid oral product (e.g., a powder) is incorporated within a pouch.

Certain products configured for oral use are in the form of pastilles. As used herein, the term "pastille" refers to a dissolvable oral product made by solidifying a liquid or gel composition so that the final product is a somewhat hardened solid gel. The rigidity of the gel is highly variable. Certain products can exhibit, for example, one or more of the following characteristics: crispy, granular, chewy, syrupy, pasty, fluffy, smooth, and/or creamy. In certain embodiments, the desired textural property can be selected from the group consisting of adhesiveness, cohesiveness, density, dryness, fracturability, graininess, gumminess, hardness, heaviness, moisture absorption, moisture release, mouthcoating, roughness, slipperiness, smoothness, viscosity, wetness, and combinations thereof.

The products comprising the emulsions of the present disclosure may be dissolvable. As used herein, the terms "dissolve," "dissolving," and "dissolvable" refer to compositions having aqueous-soluble components that interact with moisture in the oral cavity and enter into solution, thereby causing gradual consumption of the product. According to one aspect, the dissolvable product is capable of lasting in the user's mouth for a given period of time until it completely dissolves. Dissolution rates can vary over a wide range, from about 1 minute or less to about 60 minutes. For example, fast release compositions typically dissolve and/or release the active substance in about 2 minutes or less, often about 1 minute or less (e.g., about 50 seconds or less, about 40 seconds or less, about 30 seconds or less, or about 20 seconds or less). Dissolution can occur by any means, such as melting, mechanical disruption (e.g., chewing), enzymatic or other chemical degradation, or by disruption of the interaction between the components of the composition. In some embodiments, the product can be meltable as discussed, for example, in US Patent App. Pub. No. 2012/0037175 to Cantrell et al. In other embodiments, the products do not dissolve during the product's residence in the user's mouth. In some embodiments, the oral product may be in the form of a powder. The powder may be a free-flowing powder. The powder may be contained in loose form within a container, and may thus be used in a form similar to tobacco snuff where the user takes a pinch of powder from the container and places the powder in the oral cavity. Alternatively or additionally, the powder may be incorporated into a moisture-permeable (e.g., saliva-permeable) pouch, similar to a snus-type product. The pouched product may be configured for insertion into the oral cavity of a user.

In accordance with some embodiments described herein, there is provided a pouched oral product comprising a saliva permeable pouch and an oral product as defined herein incorporated within the pouch.

In some embodiments, the product of the present disclosure is in the form of a pouched oral product. Such a pouched product comprises the solid oral product containing the emulsion as described herein, disposed within a moisture-permeable container (e.g., a water-permeable pouch or saliva-permeable pouch). For example, the pouched product may comprise the solid oral product in a powder form incorporated within the saliva-permeable pouch.

Therefore, according to some embodiments described herein, there is provided a pouched oral product comprising a saliva permeable pouch and an oral product incorporated within the pouch, wherein the oral product is in powder form and comprises an emulsion that comprises a continuous phase and a dispersed phase, and wherein the emulsion comprises a cannabinoid.

Such compositions in the moisture-permeable pouch format are typically used by placing one pouch containing the composition in the mouth of a human subject/user. Generally, the pouch is placed somewhere in the oral cavity of the user, for example under the lips, in the same way as moist snuff products are generally used. The pouch preferably is not chewed or swallowed. Exposure to saliva then causes some of the components of the composition therein (e.g., flavoring agents and/or active ingredients) to pass through e.g., the moisture-permeable pouch and provide the user with flavor and satisfaction, and the user is not required to spit out any portion of the composition. After about 10 minutes to about 60 minutes, typically about 15 minutes to about 45 minutes, of use/enjoyment, substantial amounts of the composition have been ingested by the human subject, and the pouch may be removed from the mouth of the human subject for disposal.

Accordingly, in certain embodiments, the emulsion as disclosed herein and any other components noted above are combined within a moisture-permeable packet or pouch that acts as a container for use of the composition to provide a pouched product configured for oral use. Certain embodiments of the disclosure will be described with reference to FIG. 1 of the accompanying drawing, and these described embodiments involve snus-type products having an outer pouch and containing a composition as described herein. As explained in greater detail below, such embodiments are provided by way of example only, and the pouched products of the present disclosure can include the composition in other forms. The composition/construction of such packets or pouches, such as the container pouch 102 in the embodiment illustrated in FIG. 1, may be varied. Referring to FIG. 1, there is shown a first embodiment of a pouched product 100. The pouched product 100 includes a moisture-permeable container in the form of a pouch 102, which contains an oral product 104 that comprises a cellulose material and a cannabinoid as described herein.

In some embodiments, the pouch is saliva-permeable. This means that the pouch is made of a saliva-permeable pouch material. In some embodiments, the pouch material is a fleece material. In some embodiments, the pouch material is a non-woven material. In some embodiments, the pouch material is a non-woven fleece material. In some embodiments, the pouch material comprises viscose, such as viscose rayon fibers. In some embodiments, the pouch material comprises regenerated cellulose fibers. In some embodiments, the pouch material comprises polyester fibers; the polyester fibers may constitute the pouch material or may be included in combination with viscose (such as regenerated cellulose fibers).

In some embodiments, the pouch material comprises a binder that provides for heat sealing of the pouches during manufacture. In some embodiments, the pouch material comprises an acrylic binder. In some embodiments, the pouch material comprises an acrylic binder in combination with viscose and/or polyester fibers.

Suitable packets, pouches or containers of the type used for the manufacture of smokeless tobacco products are available under the tradenames CatchDry, Ettan, General, Granit, Goteborgs Rape, Grovsnus White, Metropol Kaktus, Mocca Anis, Mocca Mint, Mocca Wintergreen, Kicks, Probe, Prince, Skruf and TreAnkrare. The composition may be contained in pouches and packaged, in a manner and using the types of components used for the manufacture of conventional snus types of products. The pouch provides a moisture-permeable container of a type that may be considered to be similar in character to the mesh-like type of material that is used for the construction of a tea bag. Components of the composition readily diffuse through the pouch and into the mouth of the user.

Non-limiting examples of suitable types of pouches are set forth in, for example, U.S. Pat. No. 5,167,244 to Kjerstad and U.S. Pat. No. 8,931,493 to Sebastian et al.; as well as US Patent App. Pub. Nos. 2016/0000140 to Sebastian et al.; 2016/0073689 to Sebastian et al.; 2016/0157515 to Chapman et al.; and 2016/0192703 to Sebastian et al., each of which is incorporated herein by reference. Pouches can be provided as individual pouches, or a plurality of pouches (e.g., 2, 4, 5, 10, 12, 15, 20, 25 or 30 pouches) can be connected or linked together (e.g., in an end-to-end manner) such that a single pouch or individual portion can be readily removed for use from a one-piece strand or matrix of pouches. The pouch may be formed of a moisture-permeable non-woven fabric, such as viscose for example.

An example pouch may be manufactured from materials, and in such a manner, such that during use by the user, the pouch undergoes a controlled dispersion or dissolution. Such pouch materials may have the form of a mesh, screen, perforated paper, permeable fabric, or the like. For example, pouch material manufactured from a mesh-like form of rice paper, or perforated rice paper, may dissolve in the mouth of the user. As a result, the pouch and composition each may undergo complete dispersion within the mouth of the user during normal conditions of use, and hence the pouch and composition both may be ingested by the user. Other examples of pouch materials may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the composition contents permeate through the pouch material prior to the time that the pouch undergoes loss of its physical integrity. If desired, flavoring ingredients, disintegration aids, and other desired components, may be incorporated within, or applied to, the pouch material.

The amount of the oral product contained within each pouched product unit, for example, a pouch, may vary. In some embodiments, the weight of the composition containing the emulsion within each pouch is at least about 50 mg, for example, for example, from about 50 mg to about 2 grams, from about 100 mg to about 1.5 grams, or from about 200 to about 700 mg. In some smaller embodiments, the weight of the composition within each pouch may be from about 100 mg to about 300 mg. For a larger embodiment, the weight of the material within each pouch may be from about 300 mg to about 700 mg. If desired, other components can be contained within each pouch. For example, at least one flavored strip, piece or sheet of flavored water dispersible or water soluble material (e.g., a breath-freshening edible film type of material) may be disposed within each pouch along with or without at least one capsule. Such strips or sheets may be folded or crumpled in order to be readily incorporated within the pouch. See, for example, the types of materials and technologies set forth in U.S. Pat. No. 6,887, 307 to Scott et al. and U.S. Pat. No. 6,923,981 to Leung et al.; and The EFSA Journal (2004) 85, 1-32; which are incorporated herein by reference.

In accordance with some embodiments described herein, there is provided a package containing an oral product as defined herein or at least one pouched oral product as defined herein.

According to some embodiments described herein, there is provided a package containing an oral product as described herein. For example, the package may contain the oral product in powdered form. In such embodiments, the package may be in the form of a tin or plastic container. Alternatively or additionally, the package may contain the oral product in the form of a lozenge, pastille, tablet, or the like. The package may be in the form of a blister pack, tin or plastic container containing such solid oral dosage forms.

According to some embodiments described herein, there is provided a package containing at least one pouched oral product as described herein. A pouched product as described herein can be packaged within any suitable inner packaging material and/or outer container. See also, for example, the various types of containers for smokeless types of products that are set forth in U.S. Pat. No. 7,014,039 to Henson et al.; U.S. Pat. No. 7,537,110 to Kutsch et al.; U.S. Pat. No. 7,584,843 to Kutsch et al.; U.S. Pat. No. 8,397,945 to Gelardi et al., D592,956 to Thiellier; D594,154 to Patel et al.; and D625,178 to Bailey et al.; US Pat. Pub. Nos. 2008/0173317 to Robinson et al.; 2009/0014343 to Clark et al.; 2009/0014450 to Bjorkholm; 2009/0250360 to Bellamah et al.; 2009/0266837 to Gelardi et al.; 2009/0223989 to Gelardi; 2009/0230003 to Thiellier; 2010/0084424 to Gelardi; and 2010/0133140 to Bailey et al; 2010/0264157 to Bailey et al.; and 2011/0168712 to Bailey et al. which are incorporated herein by reference. For example, the package may be a tin or plastic container which contains a plurality of the pouched oral products.

It has been surprisingly found by the present inventors that, when a cannabinoid is included in an oral product in the form of a nanoemulsion as obtained herein, the release characteristics and rate of absorption of the cannabinoid into the oral mucosa are improved. As the skilled person will appreciate, cannabinoids are hydrophobic compounds that are not readily soluble in water. This is especially true for CBD isolate in crystalline form. Previous cannabinoid-containing oral formulations therefore suffer from the drawback that the cannabinoid is not readily released from such formulations when inserted into the mouth of the user. Moreover, due to its inherent lack of solubility, the cannabinoid was not readily absorbed into the oral mucosa. Rather, in such formulations, the user had to swallow the non-absorbed cannabinoid so as to deliver the cannabinoid to the digestive tract of the user where it could be broken down and absorbed.

It has now been found by the inventors that, by including the cannabinoid in an emulsion, the problems associated with lack of water solubility are overcome. The cannabinoid is released from the oral product and into the mouth of the user within a relatively short period of time. Furthermore, the cannabinoid is readily absorbed into the oral mucosa, and thus into the bloodstream, without the need for swallowing the active agent. The physiological effects of the active are therefore felt much more rapidly by the user than with previously known formulations.

In some embodiments, when placed in the oral cavity of a user, the oral product releases at least 50% by weight of the cannabinoid within at the most about 60 minutes, such as at the most about 45 minutes, such as at the most about 30 minutes, such as at the most about 15 minutes, such as at the most about 10 minutes, such as at the most about 5 minutes. In some embodiments, when placed in the oral cavity of a user, the oral product releases at least 60% by weight of the cannabinoid within at the most about 60 minutes, such as at the most about 45 minutes, such as at the most about 30 minutes, such as at the most about 15 minutes, such as at the most about 10 minutes, such as at the most about 5 minutes. In some embodiments, when placed in the oral cavity of a user, the oral product releases at least 70% by weight of the cannabinoid within at the most about 60 minutes, such as at the most about 45 minutes, such as at the most about 30 minutes, such as at the most about 15 minutes, such as at the most about 10 minutes, such as at the most about 5 minutes. In some embodiments, when placed in the oral cavity of a user, the oral product releases at least 80% by weight of the cannabinoid within at the most about 60 minutes, such as at the most about 45 minutes, such as at the most about 30 minutes, such as at the most about 15 minutes, such as at the most about 10 minutes, such as at the most about 5 minutes. In some embodiments, when placed in the oral cavity of a user, the oral product releases at least 90% by weight of the cannabinoid within at the most about 60 minutes, such as at the most about 45 minutes, such as at the most about 30 minutes, such as at the most about 15 minutes, such as at the most about 10 minutes, such as at the most about 5 minutes. In some embodiments, when placed in the oral cavity of a user, the oral product releases at least 95% by weight of the cannabinoid within at the most about 60 minutes, such as at the most about 45 minutes, such as at the most about 30 minutes, such as at the most about 15 minutes, such as at the most about 10 minutes, such as at the most about 5 minutes.

The rate of release into the oral cavity may be measured using an in vitro dissolution test. The dissolution profile of the cannabinoid may be measured as the amount of cannabinoid released after a certain period of time in 1 litre of phosphate buffer and at a pH of about 7.4 maintained at 37° C. using a USP paddle dissolution apparatus.

In some embodiments, at least 30% by weight of the released cannabinoid (i.e., that which has been released into the oral cavity of the user over the period of time specified) is absorbed into the oral mucosa within at the most about 60 minutes, such as at the most about 45 minutes, such as at the most about 30 minutes, such as at the most about 15 minutes, such as at the most about 10 minutes, such as at the most about 5 minutes. In some embodiments, at least 40% by weight of the released cannabinoid (i.e., that which has been released into the oral cavity of the user over the period of time specified) is absorbed into the oral mucosa within at the most about 60 minutes, such as at the most about 45 minutes, such as at the most about 30 minutes, such as at the most about 15 minutes, such as at the most about 10 minutes, such as at the most about 5 minutes. In some embodiments, at least 50% by weight of the released cannabinoid (i.e., that which has been released into the oral cavity of the user over the period of time specified) is absorbed into the oral mucosa within at the most about 60 minutes, such as at the most about 45 minutes, such as at the most about 30 minutes, such as at the most about 15 minutes, such as at the most about 10 minutes, such as at the most about 5 minutes. In some embodiments, at least 60% by weight of the released cannabinoid (i.e., that which has been released into the oral cavity of the user over the period of time specified) is absorbed into the oral mucosa within at the most about 60 minutes, such as at the most about 45 minutes, such as at the most about 30 minutes, such as at the most about 15 minutes, such as at the most about 10 minutes, such as at the most about 5 minutes. In some embodiments, at least 70% by weight of the released cannabinoid (i.e., that which has been released into the oral cavity of the user over the period of time specified) is absorbed into the oral mucosa within at the most about 60 minutes, such as at the most about 45 minutes, such as at the most about 30 minutes, such as at the most about 15 minutes, such as at the most about 10 minutes, such as at the most about 5 minutes. In some embodiments, at least 75% by weight of the released cannabinoid (i.e., that which has been released into the oral cavity of the user over the period of time specified) is absorbed into the oral mucosa within at the most about 60 minutes, such as at the most about 45 minutes, such as at the most about 30 minutes, such as at the most about 15 minutes, such as at the most about 10 minutes, such as at the most about 5 minutes.

In some embodiments, the oral product releases the cannabinoid such that at least about 20% by weight of the cannabinoid is absorbed into the oral mucosa (e.g., gingival or buccal mucosa) of the user within at the most about 60 minutes, such as at the most about 45 minutes, such at the most about 30 minutes, such as at the most about 15 minutes, such as at the most about 10 minutes, such as at the most about 5 minutes. In some embodiments, the oral product releases the cannabinoid such that at least about 25% by weight of the cannabinoid is absorbed into the oral mucosa of the user within at the most about 60 minutes, such as at the most about 45 minutes, such as at the most about 30 minutes, such as at the most about 15 minutes, such as at the most about 10 minutes, such as at the most about 5 minutes. In some embodiments, the oral product releases the cannabinoid such that at least about 30% by weight of the cannabinoid is absorbed into the oral mucosa of the user within at the most about 60 minutes, such as at the most about 45 minutes, such as at the most about 30 minutes, such as at the most about 15 minutes, such as at the most about 10 minutes, such as at the most about 5 minutes. In some embodiments, the oral product releases the cannabinoid such that at least about 40% by weight of the cannabinoid is absorbed into the oral mucosa of the user within at the most about 60 minutes, such as at the most about 45 minutes, such as at the most about 30 minutes, such as at the most about 15 minutes, such as at the most about 10 minutes, such as at the most about 5 minutes. In some embodiments, the oral product releases the cannabinoid such that at least about 50% by weight of the cannabinoid is absorbed into the oral mucosa of the user within at the most about 60 minutes, such as at the most about 45 minutes, such as at the most about 30 minutes, such as at the most about 15 minutes, such as at the most about 10 minutes, such as at the most about 5 minutes.

The percentage amount of absorption may be measured in vitro. For example, the extent of absorption of the cannabinoid into the oral mucosa may be measured via octanol-water partitioning. For example, the product may be dissolved in saliva at about 37° C., and then extracted using octanol as part of a liquid-liquid extraction step. The percentage amount of active ingredient absorbed into the oral mucosa (i.e., degree of in vitro absorption) thus corresponds to the percentage amount that is extracted into the octanol.

Release characteristics and rates of absorption of the cannabinoid into the oral mucosa may be measured by any suitable means. For example, techniques known to one skilled in the art for the measurement of release and absorption of nicotine may be used.

It was also surprisingly found that the oral product comprising an emulsion may be both chemically and physically stable for a period of at least 6 months, for example at a relative humidity of 50%. By "chemically and physically stable", it is understood that the cannabinoid does not migrate out of the product as such a migration will lead to a marked loss of the cannabinoid in the product (chemical stability), and also that no visible changes are observed over the measured period (physical stability) and the dissolution profile does not change.

It is desirable for the product to have a shelf-life such that it can be stored for a period of several days, weeks or months. Therefore, in some embodiments, the oral product is configured such that the water activity is no greater than about 0.85, such as no greater than about 0.8, such as no greater than about 0.75, such as no greater than about 0.7, such as no greater than about 0.6, such as no greater than about 0.5. It was found by the present inventors that, when the water activity of the oral product was reduced to below 0.85, the oral product could be stored for a period of several weeks or months without exhibiting significant microbiological growth.

As described herein, the "water activity" (aw) of the oral product is the partial vapor pressure of the water in the product divided by the standard state partial vapor pressure of water. Water activity may be calculated using the following formula:

$$a_w = \frac{\rho}{\rho^*}$$

where $\rho$ is the partial vapor pressure of water in the product, and $\rho^*$ is the partial vapor pressure of pure water at the same temperature. The water activity may be measured using any known and suitable measurement method in the art. In some embodiments, the water activity is measured using a resistive electrolytic hygrometer. In some embodiments, the water activity is measured using a capacitance hygrometer. In some embodiments, the water activity is measured using a dew point hygrometer. In some embodiments, the water activity is measured using a water activity meter having a tunable diode laser.

Process for Preparing Oral Product

As described herein, the oral product may be prepared using a process comprising:

(a) forming the nanoemulsion via the process as defined hereinabove; and (b) processing the nanoemulsion in order to provide an oral product.

In some embodiments, (b) processing the emulsion to provide an oral product in solid form comprises combining the nanoemulsion with a filler. The filler may be as described hereinabove. For example, in some embodiments, the filler may be a cellulose material, such as microcrystalline cellulose. In some embodiments, the filler may be present in an amount of at least 50% by weight of the oral product.

In some embodiments, the process further comprises (a)(i) of combining a filler (such as a cellulose material, such as microcrystalline cellulose) with a salt, sweetener and/or flavoring agent. The emulsion may then be combined with the resultant product from (a)(i) during (b) in order to form the oral product.

The manner by which the various components of the composition are combined may vary. As such, the overall composition with e.g., powdered composition components may be relatively uniform in nature. The components noted above, which may be in liquid or dry solid form, can be admixed in a pretreatment prior to mixture with any remaining components of the composition, or simply mixed together with all other liquid or dry ingredients. The various components of the composition may be contacted, combined, or mixed together using any mixing technique or equipment known in the art. Any mixing method that brings the composition ingredients into intimate contact can be used, such as a mixing apparatus featuring an impeller or other structure capable of agitation. Examples of mixing equipment include casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See also, for example, the types of methodologies set forth in U.S. Pat. No. 4,148,325 to Solomon et al.; U.S. Pat. No. 6,510,855 to Korte et al.; and U.S. Pat. No. 6,834,654 to Williams, each of which is incorporated herein by reference. In some embodiments, the components forming the composition are prepared such that the mixture thereof may be used in a molding process for forming the composition. Manners and methods for formulating compositions will be apparent to those skilled in the art. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

EXAMPLES

Aspects of the present invention are more fully illustrated by the following examples, which are set forth to illustrate certain aspects of the present invention and are not to be construed as limiting thereof.

Example 1

Preparation of Nanoemulsion

A process according to embodiments of the present disclosure is utilized in order to prepare an emulsion comprising an oil phase and a water phase, and a cannabinoid as the active ingredient.

The emulsion is prepared by mixing castor oil with an isolate of cannabidiol in a weight ratio of 3:1 to prepare the oil phase. The mixture is heated at about 70° C. for a period of about 10 minutes until the mixture has become transparent.

The aqueous phase is formed by mixing water with a preservative (sodium benzoate) and an emulsifying agent (combination of Myrj 52 and lecithin). The amount of preservative included is 0.4% by weight of the aqueous phase, and the amount of emulsifying agent is 20% by weight of the aqueous phase. Glycerine is also added to the water in an amount of 35% by weight of the aqueous phase. The components of the aqueous phase are subjected to high shear mixing for a period of 20 minutes. High shearing mixer is used to an initial emulsion prior to ultrasonic homogenization step. An Ika Ultra-turrax disperser is utilized to prepare homogenous slurry of solid ingredients in water and to fabricate the initial emulsion thereafter. Typically, 5000-15000 rpm shear rate is needed for prepare aqueous slurry and initial emulsion. The oil phase and aqueous phase are then combined in a weight ratio of 1:9 to provide mixture having the following components:

| | Raw Material | Amount (% w/w of emulsion) |
|---|---|---|
| Oil Phase | Castor Oil | 7.5 |
| | Cannabidiol | 2.5 |
| Aqueous Phase | Water | 40.14 |
| | Myrj 52 | 9 |
| | Lecithin | 9 |
| | Glycerine | 31.5 |
| | Sodium benzoate | 0.36 |

The oil phase and aqueous phases are combined via high shear mixing for a period of about 20 minutes at 30° C. or until a homogenous opaque emulsion forms.

The resulting macroemulsion is then added to an ultrasonic probe homogenizer (i.e., sonicator) feed vat and the temperature set to 30° C. The macroemulsion is flowed through the sonicator at 150 mL/min, and using instrument specific amplitude of 80 μm. The temperature leaving the sonicator does not exceed 40° C. A Fisherbrand model 505 ultrasonic homogenizer with max. 500 watt output is used for the present batch preparation. A Hielscher UIP4000hdT ultrasonic homogenizer is used for larger scale batch production. Typical operating parameters of Hielscher ultrasonic homogenizer are 15 liter/hour (flow rate), 21 to 66° C. (temperature range) and 7 hours (operation time per day). Parameters may be adjusted during productions to optimize the output and quality of the products.

The resulting nanoemulsion is then passed through a filter (1 μm) system. The resulting micelle droplet size is then determined using a Malvern 3000 or equivalent instrument.

Preparation of Oral Product

An oral product is then prepared via the following method:

1. microcrystalline cellulose, sodium chloride and acesulfame K are mixed in a paddle blender as dry ingredients
2. a flavoring agent is then sprayed onto the dry ingredients, and mixed until homogeneous
3. the emulsion prepared above is then sprayed onto the resulting mixture, and mixed until homogeneous The resultant oral product has the following components:

|  | Raw Material | Amount (% w/w of product) |
| --- | --- | --- |
|  | Microcrystalline cellulose | 55 |
|  | Sodium chloride | 3 |
|  | Acesulfame K | 1 |
|  | Flavoring Agent | 1 |
| Emulsion | Castor Oil | 3 |
|  | Cannabidiol | 1 |
|  | Water | 16.056 |
|  | Myrj 52 | 3.6 |
|  | Lecithin | 3.6 |
|  | Glycerine | 12.6 |
|  | Sodium benzoate | 0.144 |

The oral product has desirable release and absorption characteristics when placed into the oral cavity of the user.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilised and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. A process for preparing a nanoemulsion comprising at least one cannabinoid, the process comprising:
    (a) providing an oil phase containing at least one cannabinoid;
    (b) providing a water phase and combining the water phase with a polyoxyethylene stearic acid ester, lecithin, and glycerin, wherein the polyoxyethylene stearic acid ester and lecithin are present in an amount from about 10% to about 25% by weight, based on the total weight of the nanoemulsion;
    (c) combining the oil phase and water phase to form a macroemulsion; and
    (d) treating the macroemulsion to form the nanoemulsion.

2. The process of claim 1, wherein (d) comprises sonicating the macroemulsion to form the nanoemulsion.

3. The process of claim 1, wherein (d) comprises treating the macroemulsion in a homogenizer to form the nanoemulsion.

4. The process of claim 3, wherein the homogenizer is a high pressure valve homogenizer, an ultrasonic jet homogenizer or an ultrasonic probe homogenizer.

5. The process of claim 3, wherein the macroemulsion is passed through the homogenizer at a flow rate from about 100 mL/min to about 9 L/min.

6. The process of claim 3, wherein the macroemulsion is passed through the homogenizer at a temperature from about 20° C. to about 40° C.

7. The process of claim 1, wherein (d) comprises treating the macroemulsion in a microfluidizer to form the nanoemulsion.

8. The process of claim 1, wherein the process further comprises (a)(1) heating the oil phase to a temperature of at least about 50° C. and dissolving the at least one cannabinoid therein.

9. The process of claim 8, wherein (a)(1) comprises heating the oil phase to a temperature from about 60° C. to about 85° C.

10. The process of claim 1, wherein a weight ratio of the oil to the at least one cannabinoid is from about 1:1 to about 10:1.

11. The process of claim 1, wherein combining the water phase with the polyoxyethylene stearic acid ester, lecithin, and glycerin is performed via high shear mixing.

12. The process of claim 1, wherein (c) comprises combining the oil phase and the water phase via high shear mixing to form the macroemulsion.

13. The process of claim 1, wherein (c) comprises combining the oil phase and the water phase in a weight ratio from about 2:1 to about 1:10.

14. The process of claim 1, wherein the at least one cannabinoid is selected from the group consisting of cannabigerol (CBG), cannabichromene (CBC), cannabidiol (CBD), tetrahydrocannabinol (THC), cannabinol (CBN) and cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), Cannabinol propyl variant (CBNV), cannabitriol (CBO), tetrahydrocannabmolic acid (THCA), tetrahydrocannabivarinic acid (THCV A), and mixtures thereof.

15. The process of claim 1, wherein the at least one cannabinoid comprises cannabidiol.

16. The process of claim 1, wherein the oil phase comprises castor oil.

17. The process of claim 1, wherein a zeta potential of the nanoemulsion is less than about −10 mV.

18. The process of claim 1, wherein the nanoemulsion comprises droplets of the oil phase dispersed in the water phase, the droplets having an average diameter from about 1 nm to about 200 nm.

* * * * *